United States Patent [19]

Langberg et al.

[11] Patent Number: 5,772,604
[45] Date of Patent: Jun. 30, 1998

[54] METHOD, SYSTEM AND APPARATUS FOR DETERMINING PROGNOSIS IN ATRIAL FIBRILLATION

[75] Inventors: Jonathan J. Langberg, Atlanta, Ga.; Andreas Bollmann, Magdeburg, Germany

[73] Assignee: Emory University, Atlanta, Ga.

[21] Appl. No.: 818,739

[22] Filed: Mar. 14, 1997

[51] Int. Cl.$^6$ .................................................. A61B 5/046
[52] U.S. Cl. ............................................................ 600/518
[58] Field of Search ................................... 600/508, 509, 600/515, 518, 519

[56] References Cited

U.S. PATENT DOCUMENTS

| 5,404,880 | 4/1995 | Throne . |
| 5,411,530 | 5/1995 | Akhtar . |
| 5,568,809 | 10/1996 | Ben-haim . |
| 5,605,159 | 2/1997 | Smith et al. . |

OTHER PUBLICATIONS

Allessie, Mauritis A., "Reentrant Mechanisms Underlying Atrial Fibrillation," *Arrhythmia Mechanisms,* Chapter 53: 562–566 (undated).

Asano, et al., "On the Mechanism of Termination and Perpetuation of Atrial Fibrillation", *Am. J. Cardiol.,* 69:1033–8 (1992).

Asano, Y., et al., "Electrophysiologic Determinant in Ventricular Rate in Human Atrial Fibrillation," *J. Cardiovasc. Electrophysiol.* 6:5 343–349 (1995).

Baerman, et al., "Effect of bipole configuration on atrial electrograms during atrial fibrillation," *Pacing & Clinical Electrophysiology,* 13(1):78–87 (1990).

Boahene, et al., "Termination of Acute Atrial Fibrillation in the Wolff–Parkinson–White Syndrome by Procainamide and Propafenone: Importance of Atrial Fibrillatory Cycle Length," *J. Am. Coll. Cardiol.,* 16:1408–14 (1990).

Bogousslavsky, J. et al., "Pathogenesis of Anterior Circulation Stroke in Patients with Nonvalvular Atrial Fibrillation: The Laussanne Stroke Registry," *Neurology* 40: 1046–1050 (1990).

Bollmann, et al., "Frequency Analysis of Human Atrial Fibrillation Using the Surface ECG," *18th Annual Scientific Sessions,* North American Society of Pacing and Electrophysiology, Abstract (1996).

Botteron and Smith, "Quantitative Assessment of the Spatial Organization of Atrial Fibrillation in the Intact Human Heart," *Circulation,* 93(3):513–518 (1996).

Buchanan, L.V., et al., "Experimental Proarrhythmia with the New Class III Agent Ibutilide Fumerate: Potential Therapeutic Interventions," *Circulation, Abstracts from the 69th Scientific Sessions,* New Orleans, Louisiana 94:8(suppl.):1–191, No. 1110 (1996).

Capucci, Alessandro, et al., "Dynamic Electrophysiological Behavior of Human Atria During Paroxysmal Atrial Fibrillation," *Circulation,* 92(5):1193–1202 (1995).

Cobbe, S.M., "Incidence and Risks Associated with Atrial Fibrillation," *PACE* 17:1005–1010 (1994).

Cosio, F., "Electrophysiology, Pacing, and Arrhythmia, Atrial Vulnerability," *Clin. Cardiol.* 15:198–202 (1992).

(List continued on next page.)

*Primary Examiner*—Scott M. Getzow
*Attorney, Agent, or Firm*—Kilpatrick Stockton LLP

[57] ABSTRACT

A system, apparatus and method for determining prognosis in atrial fibrillation non-invasively detects electrical activity of the heart with external electrodes, such as with ECG leads. The diagnostic system, apparatus and method provide a non-invasive technique to classify the severity of atrial fibrillation according to peak frequency of the fibrillation, and provide useful information for treatment of the atrial fibrillation, including the prediction of conversion with ibutilide, and the estimation of time to recurrence after cardioversion.

79 Claims, 13 Drawing Sheets

OTHER PUBLICATIONS

DiMarco, J.P., "Cardioversion of Atrial Flutter by Intravenous Ibutilide. A New Class III Antiarrhythmic Agent," *J. Am. Coll. Cardiol.* 17(2):324A (1991).

Flaker, G.C., "Antiarrhythmic Drug Therapy and Cardiac Mortality in Atrial Fibrillation," *J. Amer. Coll. Cardiol.* 20:527–532 (1992).

Fujiki, A., et al., "Paroxysmal Atrial Fibrillation with and without Primary Atrial Vulnerability. Clinical and Electrophysiological Differences," *J. Electrocardiol.* 22:153–158 (1989).

Gibson, J.K., et al., "Ibutilide, a Class II Antiarrhythmic Agent, Rapidly Terminates Sustained Atrial Flutter in a Canine Model," *Pharmacologist* 34(3):165 (1992).

Harada, et al., "Atrial Activation During Chronic Atrial Fibrillation in Patients With Isolated Mitral Valve Disease," *Ann. Thorac. Surg.,* 61:104–12 (1996).

Holm, M., et al., "Noninvasive Assessment of the Atrial Cycle Length During Chronic Atrial Fibrillation in Man," *Circulation, Abstracts from the 69th Scientific Sessions,* New Orleans, Louisiana 94:8(suppl): 1–69, No. 0394 (1996).

Konings, et al., "High–Density Mapping of Electrically Induced Atrial Fibrillation in Humans," *Circulation,* 89:1665–80 (1994).

Lee, K.S., et al., "Membrane activity of class III antiarrhythmic compounds; a comparison between ibutilide, d–sotalol, E–4031, sematilide and dofetilide,"*Eur. J. Pharmacol.,* 234: 43 (1993).

Li, et al., "Distribution of Atrial Electrogram Types During Atrial Fibrillation: Effect of Rapid Atrial Pacing and Intercaval Junction Ablation," *J. Am. Coll. Cardiol.,* 27:1713–21 (1996).

Li, et al., "Clinical Significance of Fibrillatory Wave Amplitude," *Chest,* 108(2):359–363 (1995).

Maglio, C., et al., "Health Care Utilization and Cost of Care in Patients in Symptomatic Atrial Fibrillation," *Circulation, Abstracts from the 69th Scientific Sessions* 94:8(suppl):1–169, No. 0981 (1996).

Manolio, T.A., et al., "Cardiac Arrhythmias on 24–Hour Ambulatory Electrocardiography in Older Women and Men: The Cardiovascular Health Study," *J. Am. Coll. Cardiol.* 23:916–925 (1994).

Moe, G.K., "On the Multiple Wavelet Hypothesis of Atrial Fibrillation," *Arch. Int. Pharmacodyn* 1–2:183–188 (1962).

Pollick, C., "Assessment of Left Atrial Appendage Function by Transesophageal Echocardiography. Implications for the Development of Thrombus," *Circulation* 84:223–231 (1991).

Rabinovitch, "Undiagnosed Chest Pain: Determining the Cause," *Wellness* (undated).

Sih, et al., "Observations From Intraatrial Recordings on the Termination of Electrically Induced Atrial Fibrillation In Humans," *PACE,* 17:1231–1242 (1994).

Slocum, et al., "Computer Discrimination of Atrial Fibrillation and Regular Atrial Rhythms from Intra–Atrial Electrograms," *PACE,* 11:610–621 (1988).

Slocum, et al., "Diagnosis of Atrial Fibrillation From Surface Electrocardiograms Based on Computer–detected Atrial Activity," *J. of Electrocardiology,* 25(1):1–8(1992).

Slocum and Ropella, "Correspondence Between The Frequency Domain Characteristics Simultaneous Surface and Intra–Atrial Recordings of Atrial Fibrillation," *Computer in Cardiology,* 781–784 (1994).

Wells, et al., "Characterization of Atrial Fibrillation in Man: Studies Following Open Heart Surgery," *Pacing Clin. Electrophysiol.,* 1(4):426–38 (1978).

Wijffels, Maurits, et al., "Atrial Fibrillation Begets Atrial Fibrillation: A Study in Awake Chronically Instrumeted Goats," *Circulation,* 92(7):1954–1968 (1995).

Wolf, P.A., et al., "Atrial Fibrillation: A Major Contributor to Stroke in the Elderly: The Framingham Study," *Arch. Intern. Med.* 147:1561–1564 (1987).

Yelich, M., et al., "Parasympathetic Influence on Atrial Vulnerability in the Puppy,"*Am. J. Physiol.,* 235: H683–689 (1978).

"Acute Treatment of Atrial Fibrillation and Flutter: Ibutilide in Perspective," *The American Journal of Cardiology,* pp. 1–52 (1996) (Editors: Waldo and Pratt, Excerpta Medica, Inc.).

"The National Heart, Lung, and Blood Institute Working Group on Atrial Fibrillation. Atrial Fibrillation: Current Understandings and Research Imperatives," *J. Am. Coll. Cardiol.,* 7:1830–1834 (1993).

"Atrial Fibrillation," *American Heart Association Home, Health & Family Heart & Stroke A–Z Guide* (1996).

"Atrial fibrillation associated with higher mortality, costs," *American Heart Association National Center News Media,* Nov. 13, 1995, NR 95–4337 (Wolf/Benjamin)(abstract #0662 & 0663).

METHOD, SYSTEM AND APPARATUS FOR DETERMINING PROGNOSIS IN ATRIAL FIBRILLATION

FIELD OF THE INVENTION

The invention relates to a method, system and apparatus for determining prognosis in atrial fibrillation and, more particularly, to a non-invasive system and method for classifying atrial fibrillation and its response to treatment.

BACKGROUND OF THE INVENTION

The muscular contractions of the four chambers of the heart are mediated by electrical activation that proceeds through the heart in a repeating pattern. Normally, the sinoatrial node initiates each heart-beat cycle by depolarizing so as to generate an action potential. This action potential propagates relatively quickly through the atria, which react by contracting, and then relatively slowly through the atrioventricular node. From the atrioventricular node, activation propagates rapidly through the His-Purkinje system to the ventricles, which react by contracting. The rate at which the sinoatrial node depolarizes determines the rate at which the atria and ventricles contract and thus controls the heart rate. The rate at which the sinoatrial node depolarizes is regulated by the autonomic nervous system which can accelerate the heart rate so that the heart, for instance, beats at a faster rate during exercise and beats at a slower rate during rest. The above-described cycle of events holds true for a healthy heart and is termed normal sinus rhythm.

The heart, however, may have a disorder or disease that results in rapid abnormal activation that preempts sinus rhythm. Atrial fibrillation occurs when the orderly wavefront of activation breaks up into multiple components. Each of these activation wavefronts wanders rapidly and chaotically through the atria. This irregular activation pattern results in uncoordinated and ineffective contraction of the atria as well as a rapid and irregular ventricular rate.

Atrial fibrillation is associated with significant morbidity and mortality. Death rates among atrial fibrillation patients are 20 to 30 percent higher in men and 30 to 50 percent higher in women compared to matched controls. Atrial fibrillation is associated with a more than fourfold increase in risk of stroke and approximately 15 percent of all strokes occur in people with atrial fibrillation. In addition, this arrhythmia has a huge economic impact with heath care costs for these patients ranging from $6,000 to $15,000 per patient per year. Atrial fibrillation is the most common arrhythmia requiring treatment, occurring in about 2 million people in the United States and in about 10% of individuals over 70 years of age. In addition to being aware of the irregular heart activity, people afflicted with atrial fibrillation generally have symptoms of weakness, fatigue, breathlessness and chest pain.

The treatment of atrial fibrillation is difficult since both the natural history of atrial fibrillation and its response to therapy are unpredictable. Presently, arrhythmia duration and echocardiographic measurements of atrial size are used to prognosticate, but give no information regarding the electrophysiologic state of the atria.

Atrial fibrillation is caused by a reentrant mechanism which results in multiple simultaneous reentrant activation wavefronts in the atria. The average size of a reentry pathway for one of these wavefronts during atrial fibrillation is dependent on atrial wavelength, defined as the product of conduction velocity and refractory period. Longer atrial wavelengths are associated with larger and fewer wavefronts while shorter atrial wavelengths result in a greater number of smaller wavefronts. Atrial fibrillation is a progressive disorder and animal and clinical studies have shown an association between shorter wavelengths and persistent atrial fibrillation. The average frequency and degree of fractionation of intra-atrial recordings during atrial fibrillation correlate with wavelength and the size of reentry pathways.

An example of an electrocardiogram (ECG) of normal sinus rhythm is shown in FIG. 1 and is characterized by a P wave, which corresponds with atrial depolarization and contraction of the atria, followed by a QRS complex, which corresponds with depolarization and contraction of the ventricles. Due to size differences between the atria and the ventricles, the P wave is considerably smaller than the QRS complex. A T wave follows the QRS complex and corresponds to ventricular repolarization. Atrial repolarization is difficult to detect with an ECG since the atrial repolarization signal has a small amplitude and is mainly hidden by the much larger QRST complex. In addition to the P wave and the QRST complex, a normal ECG is also characterized by a PR interval, defined as the time between atrial and ventricular contractions, of about 0.12 to 0.20 seconds and regular R-R intervals, defined as the time between QRST complexes, of about 0.60 to 1 second.

In contrast to the normal sinus rhythm of FIG. 1, an example of an ECG for a patient with atrial fibrillation is shown in FIG. 2. As shown in FIG. 2, this ECG lacks P waves and instead has chaotic atrial depolarization manifested as an irregular "fibrillatory" baseline. Atrial fibrillation is also characterized by QRST complexes of a normal shape, due to normal ventricular activation sequence, but with irregular intervals.

Previous attempts to characterize atrial fibrillation based on ECG signals have been unsuccessful. One approach to classifying atrial fibrillation is by the amplitude of the fibrillatory baseline signal. For more than 35 years, coarse atrial fibrillation was thought to be associated with rheumatic mitral valve disease while fine atrial fibrillation was most often seen in patients with ischemic or hypertensive cardiomyopathy. Subsequently, more quantitative studies, however, have failed to show a consistent correlation between a large amplitude "coarse" fibrillatory baseline signal and the presence of rheumatic heart disease or left atrial enlargement. Moreover, fibrillatory baseline amplitude does not appear to be affected by atrial wavelength or to predict the behavior of the arrhythmia. The amplitude of the fibrillatory baseline signal therefore cannot be used to classify the atrial fibrillation.

Another approach to classifying atrial fibrillation has focused on the morphology of intra-cardiac electrograms. Wells et. al., in "Characterization of Atrial Fibrillation in Man: Studies Following Open Heart Surgery," *Pacing Clin Electrophysiol* 1978; 1(4):426–38, disclose the use of a single bipolar atrial electrogram recorded directly from the heart after cardiac surgery to stratify the arrhythmia into four different types. Based on Wells classification, Type I fibrillation had discrete signals with intervening isoelectric intervals, Type II fibrillation had discrete activation without any intervening periods of complete electrical quiescence, Type III fibrillation had no clear isoelectric intervals, and Type IV fibrillation was characterized as alternating between the Type I and Type III fibrillation. The clinical utility of this classification technique, however, is limited by the need for invasive recording.

Another approach to classifying atrial fibrillation is proposed by Konings et al. in "High-Density Mapping of Electrically Induced Atrial Fibrillation in Humans," *Circulation* 1994; 89:1665–80. Konings et al. disclose the classification of atrial fibrillation in patients with the Wolff-Parkinson-White syndrome undergoing cardiac surgery by using high-density intra-operative mapping of the right atrium free wall. Konings et al. categorized the arrhythmia based on the number and complexity of activation wavefronts within a particular 3.6 cm diameter region of the atrium being studied. This approach, as with the approach of Wells et al., suffers from a disadvantage that it is limited by the need for invasive recording. A further limitation of the assessments based on focal or regional activation patterns was shown by Li et. al. in "Distribution of Atrial Electrogram Types During Atrial Fibrillation: Effect of Rapid Atrial Pacing and Intercaval Junction Ablation," *J Am Coll Cardiol* 1996; 27:1713–21. Li et al. noted that all four patterns of atrial fibrillation described by Wells et. al. were present concurrently at different locations of the atria during experimental atrial fibrillation. The utility of the mapping proposed by Konings et al. is therefore doubtful.

A different approach to the classification of atrial fibrillation has focused on atrial wavelength and fibrillation frequency. An increasing body of evidence suggests that shorter atrial wavelengths are critically important for the initiation and perpetuation of atrial fibrillation. Wavelength measurements have been shown to be accurate predictors of atrial fibrillation inducibility. The persistence of atrial fibrillation and its response to antiarrhythmic drugs has also been found to be closely correlated with wavelength. Several experimental and clinical studies have shown an association between the frequency of fibrillation recorded on the intra-cardiac electrogram, the atrial wavelength, and the behavior of the arrhythmia.

For instance, Asano et al., in "On the Mechanism of Termination and Perpetuation of Atrial Fibrillation," *Am J Cardiol* 1992; 69:1033–8, induced atrial fibrillation with rapid pacing in 30 patients undergoing electrophysiologic study. The mean atrial activation interval recorded in the right atrium was well correlated with atrial wavelength; those patients having spontaneous termination of atrial fibrillation had an average fibrillation frequency of 5.6 Hz, significantly lower than the 6.4 Hz recorded in the group of patients where the arrhythmia persisted.

Boahene et. al., in "Termination of Acute Atrial Fibrillation in the Wolff-Parkinson-White Syndrome by Procainamide and Propafenone: Importance of Atrial Fibrillatory Cycle Length," *J Am Coll Cardiol* 1990; 16:1408–14, measured fibrillatory cycle length from the high right atrium in 55 patients with the Wolff-Parkinson-White syndrome. Boahene et al. also found that patients with sustained atrial fibrillation had shorter mean atrial activation intervals than did their counterparts with non-sustained atrial fibrillation.

In both experimental models of atrial fibrillation and in clinical studies, persistent rapid atrial rates have been shown to produce a marked, progressive shortening of the atrial refractory period. The decrease in refractoriness is accompanied by a comparable increase in the fibrillation frequency. This electrical remodeling is responsible for the self-perpetuating nature of atrial fibrillation and may play a major role in the natural history of the arrhythmia.

Despite an increase in the number of treatment options, the management of atrial fibrillation remains a trial and error process. The initial goal is to restore sinus rhythm. This so-called cardioversion procedure is usually accomplished though administration of a high voltage shock (about 750 VDC-2000 VDC) via paddles placed on the chest. Last year, the Food and Drug Administration approved ibutilide as an effective alternative to such electrical cardioversion of atrial fibrillation. This potent antiarrhythmic drug is administered intravenously for about 10 to about 20 minutes. This option is attractive because it may obviate the need for general anesthesia and a powerful shock. However, ibutilide is effective in less than about one third of the patients with atrial fibrillation.

Patients with persistent or recurrent atrial fibrillation require chronic therapy of their arrhythmia. Coumadin, an anticoagulant, is usually given to these patients to reduce the risk of stroke. Antiarrhythmic drugs may decrease the frequency and severity of atrial fibrillation episodes, but are incompletely effective and associated with significant side effects, including the possibility of proarrhythmia. When the risks and toxicity of antiarrhythmic drugs outweigh their potential benefit, patients are left in atrial fibrillation and palliated with medications that slow the heart rate.

New, non-pharmacological treatments of atrial fibrillation are in clinical trials. An implanted device, slightly larger than a conventional pacemaker, has been developed that automatically detects and shocks atrial fibrillation back into normal rhythm. Atrial fibrillation is also being treated experimentally with catheter ablation. With this technique, a wire is introduced into the femoral vein and advanced into the atrium. High frequency current is passed through the tip of the wire and is used to cauterize the atria. A series of long "lines" are burned into the atria, dividing it electrically into regions too small to support atrial fibrillation.

Current screening techniques have involved the use of intra-atrial electrograms, catheters, or other invasive techniques. A need therefore exists for a non-invasive assessment of the electrophysiologic state of the atria during atrial fibrillation. A need further exists for a classification of atrial fibrillation that can be performed quickly and accurately. The techniques of the present invention are suitable for the prediction of conversion with ibutilide, for estimation of time to recurrence after cardioversion, and for prediction of response to chronically administered antiarrhythmic drugs. The techniques of the present invention will identify suitable candidates for the implanted atrial defibrillator or for catheter ablation. The techniques of the present invention are also suitable for the prediction of left atrial thrombus and the risk of stroke.

Applicants provide a device for rapidly analyzing the electrical signals from the heart of a patient in atrial fibrillation, with the purpose of assessing the suitability of administering electric shock, or ibutilide, or other treatments.

SUMMARY OF THE INVENTION

Systems, methods and apparatus for determining severity or prognosis of atrial fibrillation according to the present invention are non-invasive and detect electrical activity of a heart with external electrodes, such as with ECG leads. The signals from the electrodes are filtered and amplified and then converted into digital signals. Each QRST complex within the signal is averaged with similar QRST complexes to form templates. Each QRST complex is then removed from the signal by subtracting its corresponding template. After the QRST complexes have been removed from the signal, the resultant signal, the fibrillatory baseline signal, undergoes a Fourier transformation to produce a frequency domain set of signals. The set of signals in the frequency domain are analyzed to derive a peak frequency in the spectrum.

The frequency of the peak is then used to classify the atrial fibrillation. Applicants have discovered that this peak frequency measurement is an accurate reflection of the peak frequency recorded directly from the heart. Further, this non-invasive measurement has a number of uses. With patients having persistent atrial fibrillation of uncertain duration, the peak frequency can be used to determine the length of time the arrhythmia has been present. Patients with atrial fibrillation of about 1–3 months duration have a peak frequency of about 5.6 Hz, whereas those with a duration longer than about 3 months have a peak frequency of about 6.8 Hz are Applicants have discovered that the peak frequency measurement can be used to guide the treatment of patients with atrial fibrillation. All patients with a peak frequency less than about 6.0 Hz will have successful cardioversion with ibutilide infusion, whereas only about 28% of patients with a peak frequency greater than about 6.0 Hz will so respond.

The peak frequency measurement can be used to determine the duration of normal sinus rhythm after initially successful cardioversion. Patients with a peak frequency of about 6.6 Hz are at high risk for early recurrence and may require chronic oral administration of antiarrhythmic drugs. Patients with a peak frequency of about 5.5 Hz are at low risk for early recurrence and do not need additional treatment.

BRIEF DESCRIPTION OF THE DRAWINGS

The accompanying drawings, which are incorporated in and form a part of the specification, illustrate preferred embodiments of the present invention and, together with the description, serve to explain the principles of the invention. In the drawings.

DESCRIPTION OF THE INVENTION

Atrial Fibrillation

Figure 1:
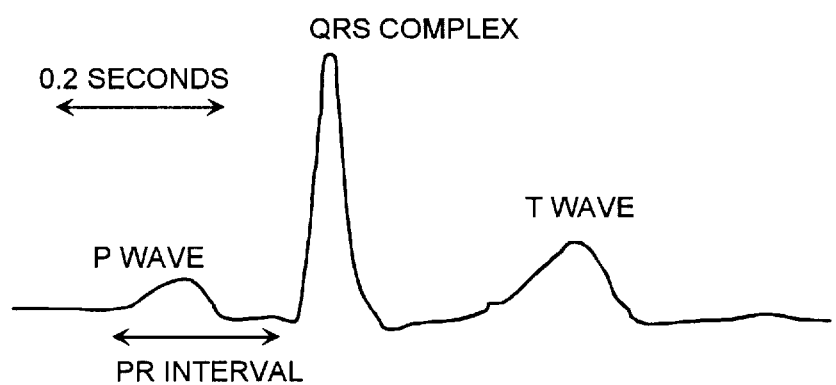
FIG. 1 is an example of an enlarged electrocardiogram from a patient in normal sinus rhythm.
Figure 2:
FIG. 2 is an example of an electrocardiogram of atrial fibrillation.

Atrial fibrillation is an arrhythmia resulting from continuous, chaotic reentry of electrical impulses within the atrial myocardium. It is advantageously compared to the turbulent waves on the surface of a pool after diving into the pool.

Atrial fibrillation is much more common than atrial flutter, and occurs in the same diseases, including rheumatic mitral valve disease, hypertension and arteriosclerotic heart diseases. Presence of atrial fibrillation sometimes indicates stretching of the left atrium. Many cases of atrial fibrillation show no evidence of such stretching.

In the conventional view of atrial fibrillation, it is generally initiated by a single atrial premature beat occurring very early during the refractory period of the atrial myocardium. This single impulse then "fragments" due to the variable refractory periods of adjacent atrial myocardium not yet fully repolarized. These partially depolarized cells then result in very slow intra-atrial conduction. Continuous reentrant excitation waves occur within both atria if excitability and refractoriness vary enough from one portion of the atrial myocardium to the next. The arrhythmia depends on a disparity between refractoriness and conduction velocity in various parts of the atrium, and, therefore, significant atrial myocardial disease must exist. The conventional mechanism is independent of S-A or A-V nodal reentry, and maneuvers or drugs affecting A-V nodal conduction generally will not change the basic rate of atrial fibrillation.

Applicants have discovered, after appropriate analysis of the electrical signals in atrial fibrillation, that, in a majority of patients, a discrete peak frequency is readily determined. The peak frequency substantially correlates inversely with the refractory period of the atrial tissue in atrial fibrillation. The peak frequency is, in turn, an accurate measure of the prognosis of the patient in atrial fibrillation, and is useful for determining the appropriate course of treatment, be it electric shock cardioversion, or intravenous administration of an antiarrhythmic drug such as ibutilide, or chronic administration of an antiarrhythmic drug or drugs before attempting cardioversion. Applicants also provide a device to be used while the patient is in atrial fibrillation to provide rapid determination of the peak frequency of atrial fibrillation occurring in the patient.

Patients in atrial fibrillation can be readily divided into those needing initial therapy, and those requiring therapy for a chronic condition. Initial therapy typically involves intravenous administration of an antiarrhythmic drug, such as ibutilide or procainamide. Alternatively, initial therapy is readily accomplished by the administration of between about 750 and about 2000 volts of direct current with an external defibrillator. Applicants have discovered that determining the peak frequency of the atrial fibrillation can guide the choice between these two types of initial therapy for the patient with atrial fibrillation. A patient in atrial fibrillation with a peak frequency of less than about 6.0 Hz has a substantially 100% probability to convert to normal sinus rhythm upon acute administration of ibutilide, whereas only about 28% of patients with a peak frequency above about 6.0 Hz will convert to normal sinus rhythm with the same treatment.

Applicants have also discovered that determining the peak frequency of the atrial fibrillation can be used to determine the duration of normal sinus rhythm after successful cardioversion. A patient in atrial fibrillation with a peak frequency of less than about 6.5 Hz will have about 80% probability of remaining in normal sinus rhythm for more than about 3 months after cardioversion, whereas a patient in atrial fibrillation with a peak frequency of more than about 6.5 Hz will have about 80% probability of recurrent atrial fibrillation within about 3 months after successful cardioversion.

Such patients having a peak frequency above about 6.5 Hz are at high risk of recurrence. These patients are generally treated with chronic oral antiarrhythmic drugs. A variety of known antiarrhythmic drugs are suitable for this purpose. Such drugs include, but are not limited to quinidine, procaineamide, disopyramide, flecainide, propafenone, sotalol, amiodarone, and ethmozine. See, e.g., Lee, K. S. et al., *Eur. J. Pharmacol* 234:43 (1993).

Illustrative Embodiments of the Present Invention

Figure 3:
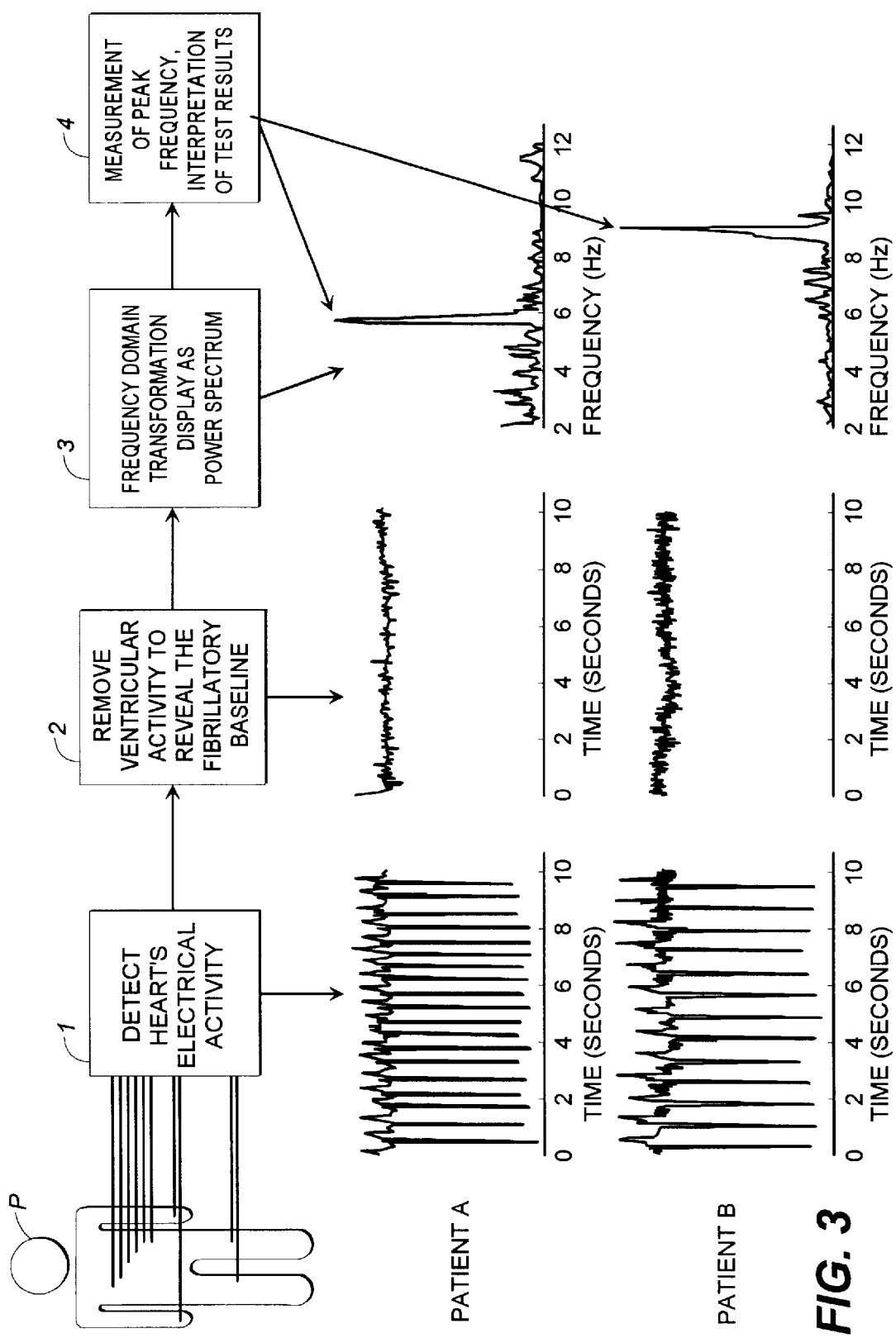
FIG. 3 is a diagram showing operations according to a preferred embodiment of the invention.

Reference will now be made in detail to the preferred embodiment of the invention, an example of which is illustrated in the accompanying drawings. An overview of the invention is depicted in FIG. 3. With the invention, a patient P has his or her heart's electrical activity detected from one or more electrodes at step 1. At a step 2, ventricular activity detected at step 1 is removed from the signal to reveal a fibrillatory baseline signal. The fibrillatory baseline signal is converted into a frequency domain signal at step 3 and results of the transformation are displayed as a power spectrum. At step 4, a peak frequency in the power spectrum is measured and results of the measurement are interpreted.

As depicted in FIG. 3, measurements of the heart's electrical activity may differ between a patient A and a patient B. The signals detected at step 1 for patients A and B, however, may appear similar and do not reveal much, if any, significant information about the atrial fibrillation. The fibrillatory baseline signals, which are the result of step 2, have been processed to isolate the fibrillatory baseline signal. It is generally not possible to quantify differences in the fibrillatory baseline signals between patients A and B by casual inspection alone. The transformation of the fibrillatory baseline signal into the frequency domain at step 3 and the measurement of the spectrum at step 4, on the other hand, demonstrate that patient A has a concentration of energy at a peak frequency of about 5.8 Hz and patient B has a concentration of energy at a peak frequency of about 9.0 Hz. As discussed in greater detail below, the frequency at which the energy has a peak strongly correlates with the severity of atrial fibrillation and therefore with the type of treatment that is best suited for the patient. In the example shown in FIG. 3, patient A would have a high probability of returning to normal sinus rhythm with acute treatment and patient B would require more aggressive therapy.

Figure 4:
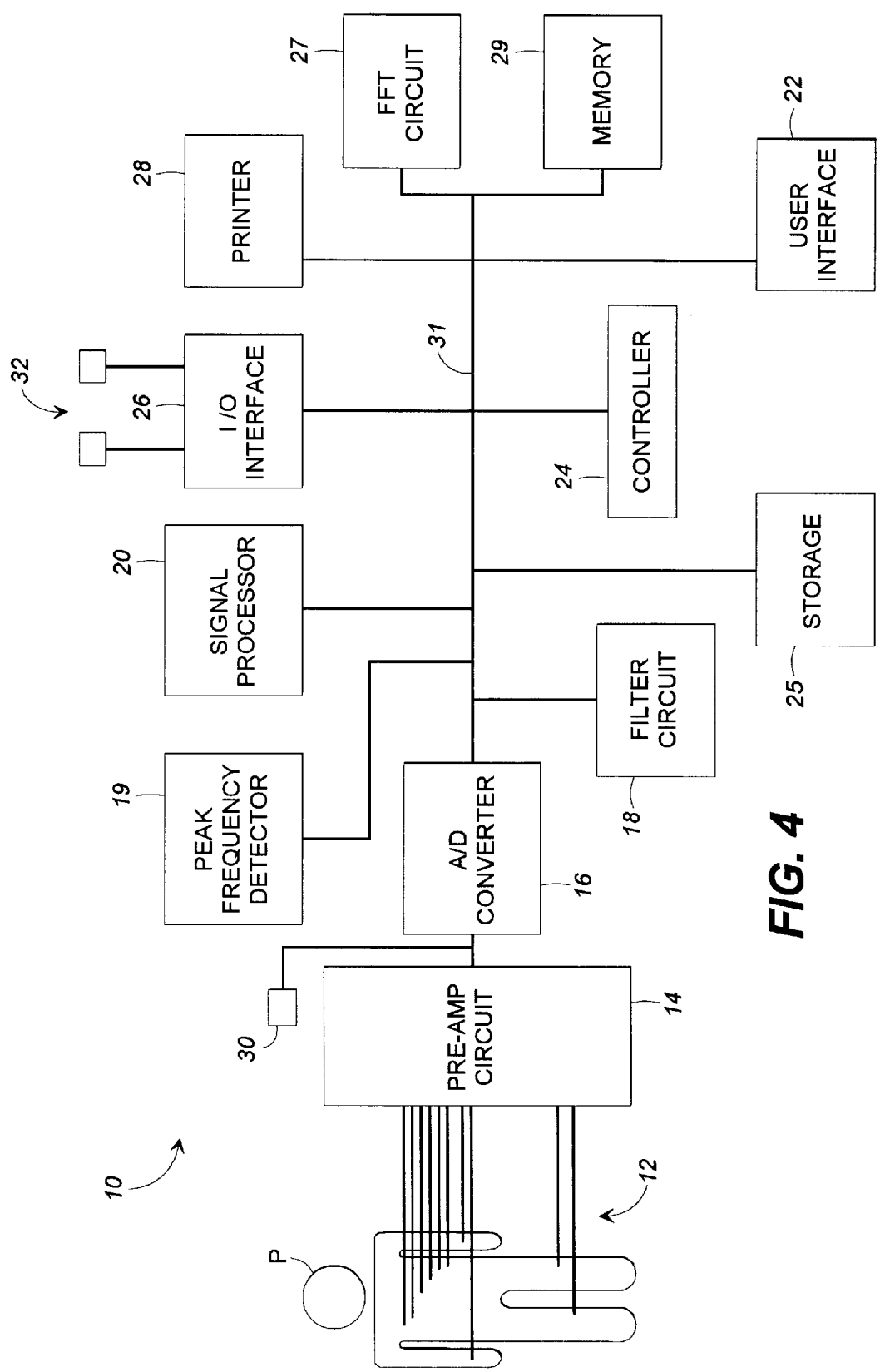
FIG. 4 is a block diagram of a diagnostic system according to a preferred embodiment of the invention.

A diagnostic system 10 according to a preferred embodiment of the invention is shown in FIG. 4. The diagnostic system 10 includes electrodes and corresponding leads 12 attached to a patient P for detecting the electrical activity of the heart. The electrodes may comprise any single electrode or combination of electrodes conventionally used to generate electrocardiograms (ECGs), such as leads aVF, V1, and V5, or they may comprise other types of skin electrodes. The electrodes 12 produce electrical signals based on the electric fields generated by the heart and these heart signals are passed through a pre-amplifier circuit 14. In addition to amplifying the heart signals, the pre-amplifier circuit 14 also includes a notch filter for removing 60 Hz interference and a bandpass filter to remove signals falling outside of a pass-band of 0.04 Hz to 100 Hz.

The signals from the pre-amplifier circuit 14 are passed to an analog-to-digital (A/D) converter 18 which converts the analog signals to digital signals. The A/D converter 18 preferably has a sampling rate of at least 1024 Hz, but may have other sampling rates. Additional analog signals, such as a high level input from an external ECG monitor, may be received at a terminal 30 and may also be processed by the A/D converter 18.

A filter circuit 18 receives the digital signals from the A/D converter 16 and provides additional filtering within a pass-band of 0.5 Hz to 60 Hz to reduce respiration-induced fluctuation in the signals and to eliminate electrical noise. Although the invention is not limited to any particular type of filter, one suitable filter is a bilinearly transformed null-phase filter, which advantageously suppresses wandering of the baseline signal. Although the filter circuit 18 has been shown as being separate from the pre-amplifier circuit 14, the filter 18 may be integrated into the pre-amplifier circuit 16.

The filtered signals output from filter circuit 18 are supplied to a bus 31 and are preferably stored within storage 25 under the control of controller 24. The storage 25 preferably comprises an optical disc recording system, such as the one manufactured by Prucka Engineering, Inc., of Houston, Tex., but may comprise any other suitable type of storage device, such as a magnetic disc drive or a cassette drive.

The diagnostic system 10 further includes a signal processor 20, a peak frequency detector 19, and a transformation circuit 27 for performing various signal processing operations upon the digital signals. The operations of the signal processor 20, peak frequency detector 19, and transformation circuit 27 will be described in more detail below with reference to FIGS. 5A to 5D. The diagnostic system 10 also comprises a printer 28 and a user interface 22, which may include a display, keyboard, mouse, and status indicators. The diagnostic system 10 includes memory 29, which may comprise random access memory (RAM), read-only memory (ROM), or a combination of RAM and ROM, for use by the controller 24, the signal processor 20, the peak frequency detector 19, and the transformation circuit 27.

The diagnostic system 10 may also include an input/output (I/O) interface 26 having a set of input and output terminals 32. In addition to receiving heart signals contemporaneously through pre-amplifier circuit 14, A/D converter 16, and filter circuit 18, the diagnostic system 10 may also receive analog heart signals from an external device through the I/O interface 26. This external device may comprise, for instance, an ECG machine, a Holter monitor equipped with a magnetic cassette for recording the heart signals, or a hospital-based ECG monitoring system. Through the I/O interface 26, the heart signals may be recorded at one time and then imported into the diagnostic system 10 for analysis. The I/O interface 26 also permits the transfer of signals and data from the diagnostic system 10 to an external device or system. For instance, results of the system 10 may be displayed on an external ECG machine.

The I/O interface 26 may also incorporate a network interface whereby the diagnostic system 10 may receive digital signals indicative of the heart's activity from any type of device or transmitter. The device, for instance, may comprise a plug-in memory or other portable device having a memory. The transmitters, for instance, may be computers within a local area network (LAN), wide area network (WAN), form part of the Internet, or computers that have dial-up access to the diagnostic system 10. By connecting to a transmitter, the I/O interface 26 allows data that has been recorded at another location, such as at another location within the same hospital or office, at a remote hospital, or at a patient's home, to be transferred to the diagnostic system 10 for analysis. Thus, rather than transporting a patient from to the diagnostic system 10 or requiring each hospital to be equipped with the diagnostic system 10, the diagnostic system 10 can quickly be made available to a great number of patients.

The operations of the diagnostic system 10 will now be described with reference to FIGS. 5A to 5D. After a patient P has been equipped with one or more of the electrodes 12, a user activates the system 10 at step 42 through the user interface 22, such as by entering a command at a keyboard or simply by pressing a switch. The system 10 responds at step 44 by receiving the analog heart signals, by passing them through pre-amplifier circuit 14 and by converting the signals into digital signals at A/D converter 16. At step 46, the digital heart signals are passed through the filter circuit 18 for band-pass filtering. Next, at step 48, the controller 24 acquires the digital signals, labels each group of signals, and then stores the signals within storage 25 or memory 29. The controller 24 preferably acquires and labels 10 second intervals of signals from the aVF, V1 and V5 leads 12, although the controller 24 can acquire and label signals from other ones of the electrodes 12 and may acquire and label signals at intervals of time other than ten seconds.

The signal processor 20, at step 50, detects and identifies the QRST complexes within the digital signals. The diagnostic system 10 is not limited to any particular sampling interval of time or to any particular number of QRST complexes. To reflect this flexibility in the diagnostic system 10, the QRST complexes have been referenced as $QRST_1$, $QRST_2$, ... $QRST_n$, where n may be 6 to 8 for a 10 second sample and may be other numbers depending upon the desired sampling time. To detect the QRST complexes, the signal processor 20 detects the maximum absolute amplitude within the signals. Based on this maximum amplitude, the signal processor identifies R waves by isolating local maximums within the signal which have amplitudes 50% or greater than that of the maximum amplitude. The system 10, however, is not limited to this particular algorithm but may use other peak detection algorithms.

Next, at step 52, the signal processor 20 measures the time duration for each QRST complex $QRST_1$, $QRST_2$, ... $QRST_n$. The duration of each QRST interval is measured by proceeding forward in time until a magnitude of the signal drops to 5% that of the peak corresponding to that particular R wave. Each QRST interval is then determined to occur from its own onset to the onset of the subsequent QRST interval. The invention is not limited to this particular algorithm but instead may incorporate other algorithms for measuring the QRST time intervals. At step 54, the QRST intervals are averaged together to derive a mean QRST interval.

Although the fundamental frequency of the QRST complex is well below a range of 4 Hz to 12 Hz which is relevant to the analysis of a fibrillatory baseline signal, the QRST complexes are preferably removed from the detected signals. Preliminary studies have revealed that harmonics arising from the QRST complex often produce more energy in the relevant frequency range than the much lower amplitude fibrillatory activity. Therefore, accurate assessment of the frequency spectrum of the atrial component requires selective attenuation of the QRST complex. In general, the QRST complex is attenuated using a template matching and subtraction technique.

Figure 5A:
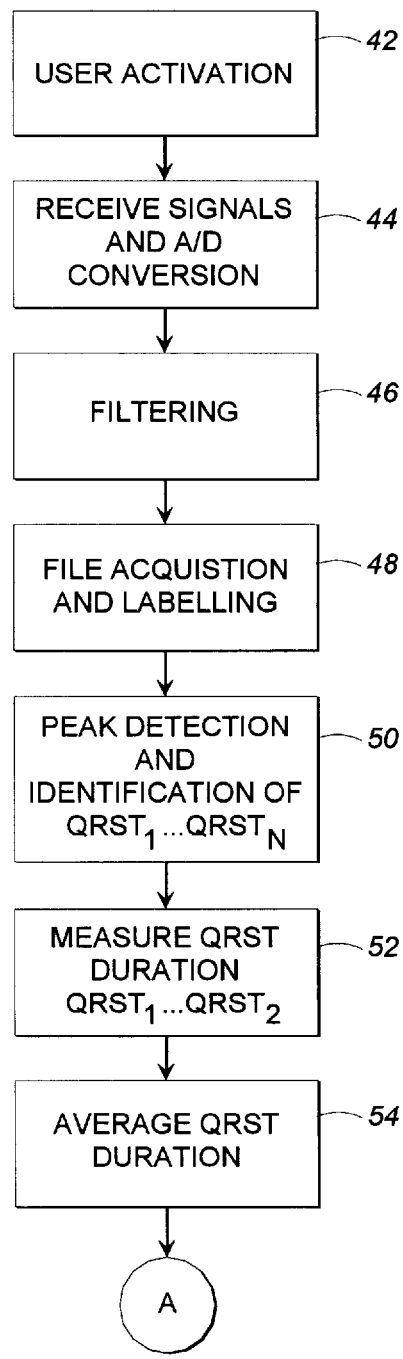
FIGS. 5A to 5D are flow charts depicting steps executed by the system shown in FIG. 4 in processing electrocardiogram signals.
Figure 5B:
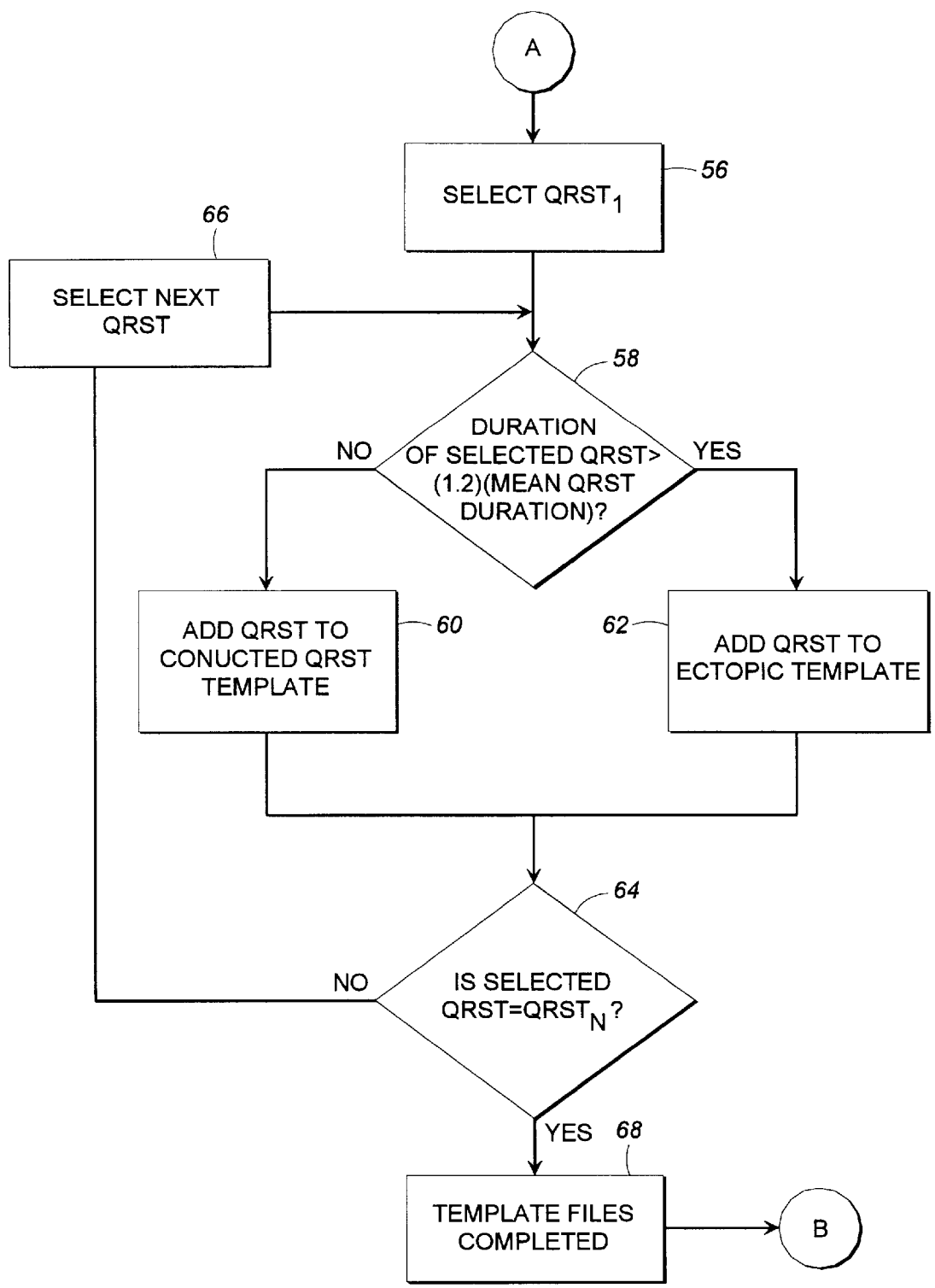

With reference to FIG. 5B, the first QRST complex of $QRST_1$ is selected at step 56 and its duration is compared to the mean duration for all QRST complexes, which has been determined at step 54. The duration of QRST, is compared to a product of 1.2 times this mean value in duration and is considered to be ectopic if greater than the product and conducted if not greater than the product. Based on the comparison at step 58, the QRST complexes are either added and averaged in with a conducted template at step 60 or an ectopic template at step 62. At step 64, the signal processor 20 determines whether the selected QRST is the last $QRST_n$ and, if it is not the last $QRST_n$, selects the next QRST at step 66 and returns to step 58. After all of the QRST complexes have been averaged together in either the conducted template or ectopic template, the controller 24 completes the template files, such as by labeling the files and placing them in storage 25 or memory 29.

Figure 5C:
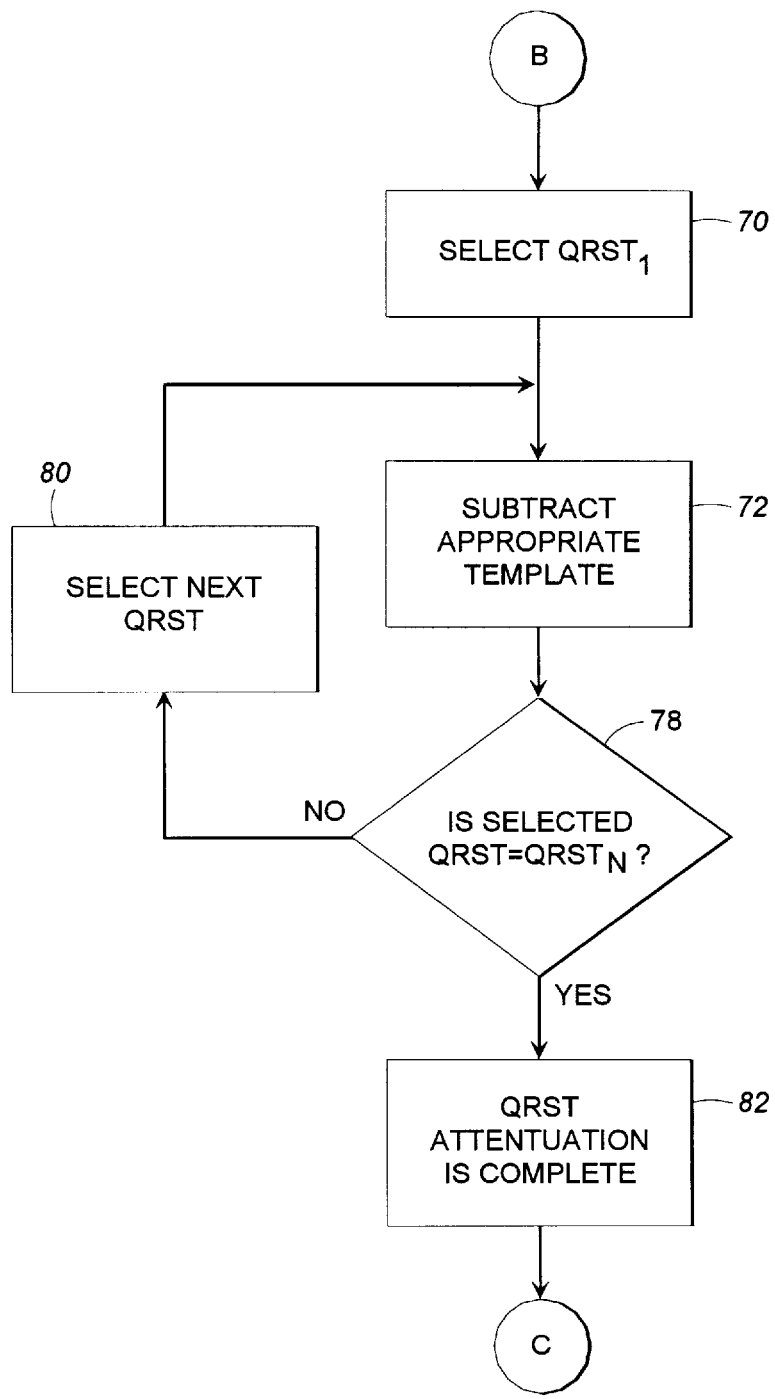

The signal processor 20 then proceeds to subtract the QRST complexes from the signals to isolate the fibrillatory baseline signal. One approach to this subtraction is shown in FIG. 5C which includes a first step 70 of selecting the first QRST complex, namely $QRST_1$. Based on the results of step 58, the signal processor 20 selects the appropriate template and subtracts that template from the signal at step 72. At step 78, the signal processor 20 determines whether the selected QRST complex is equal to the $QRST_n$ complex and, if not, selects the next QRST complex at step 80 and proceeds to subtract out the appropriate template for the next QRST complex at step 72. At step 82, the QRST attenuation is complete and the controller 24 places the isolated fibrillatory baseline signals within storage 25 or memory 29.

Figure 5D:
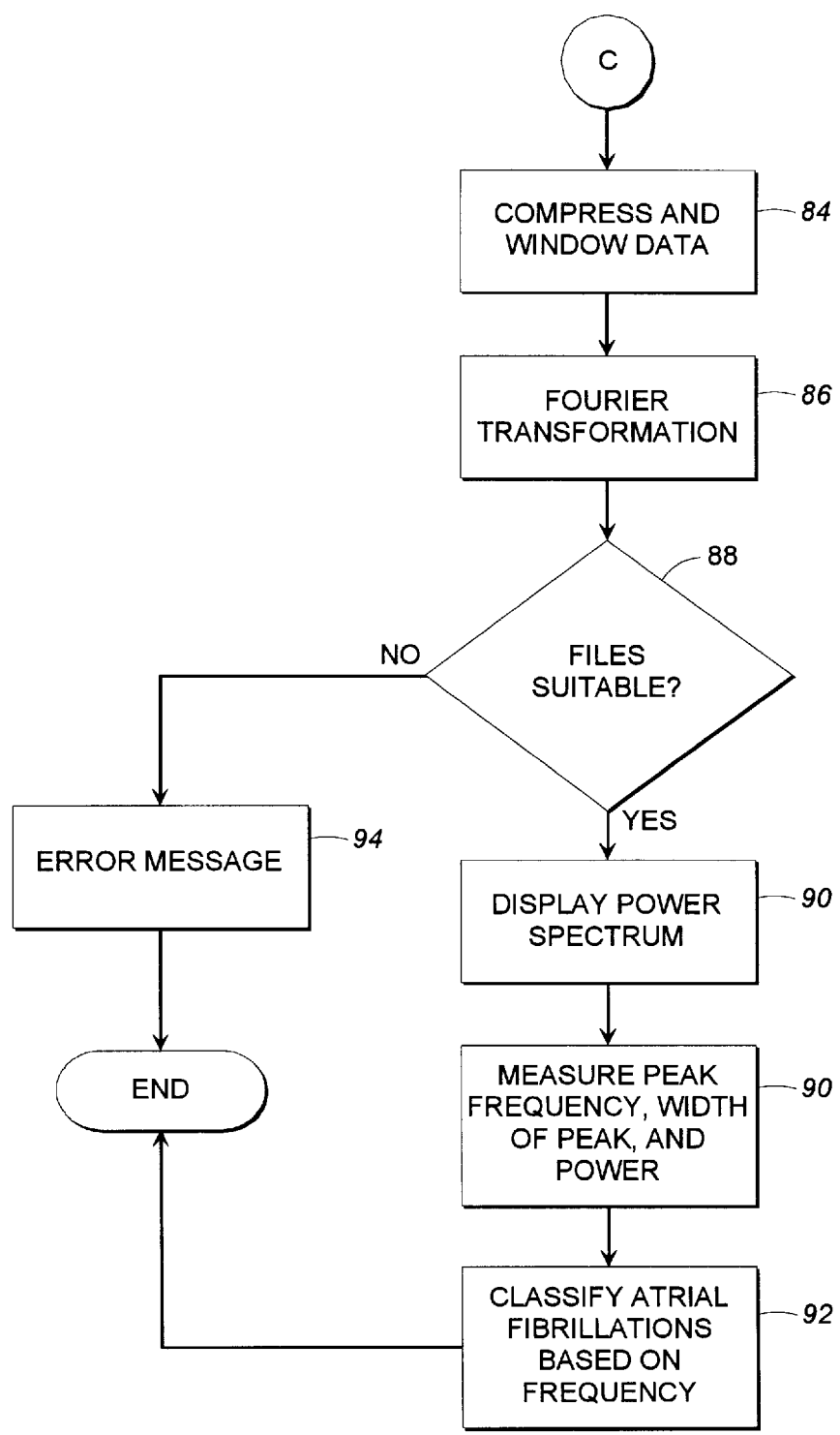

With reference to FIG. 5D, the digital signals are compressed at step 84 by decreasing the sampling rate to 102 Hz and a Hamming window or other windowing technique is applied in order to prevent the introduction of any artifacts. The sampling rate for compressing the signals, as with the sampling rate at the A/D converter 16, may be varied and is not limited to this precise rate. At step 86, the transformation circuit 27, which preferably comprises a Fast Fourier transformation circuit, transforms the fibrillatory baseline signal into a set of frequency domain signals, preferably by performing a discrete Fourier transformation. The Fourier transformation, in this example, is a 1024 point transformation but may be varied according to the duration of the signal and the desired resolution.

At step 88, the controller 24 determines whether the files are suitable. The files may not be suitable for various reasons, for instance, if the fibrillatory baseline signal is unstable or if the QRST complexes are inconsistently detected. If the files are not suitable, then at step 94 the controller 24 issues an error message at the user interface 22, such as by generating a message on a display or by lighting or flashing an indicator. The error message preferably indicates that the signals are not suitable for analysis and may provide some guidance and troubleshooting suggesting how a suitable signal sample may be acquired. For instance, the controller 24 may detect a complete absence of a signal during periods and may suggest that the user verify that each electrode 12 is securely attached to the patient P.

At step 90, the signal processor 20 calculates the power spectrum of the set of frequency domain signals by calculating a squared magnitude of each sample frequency. At step 90, the peak detector 19 measures the peak frequency in the power spectrum and also determines the degree to which the power of the signal is concentrated around the peak frequency, for instance, by measuring the width of this peak at 10% of maximal amplitude and by measuring the percentage of total power within a bandwidth of 4 to 9 Hz contained within ±0.5 Hz of the peak. The signal processor 20 may perform other measurements, such as at other percentages of power or at other bandwidths about the peak frequency, in addition to, or instead of, the ones described.

At the final step 92 in FIG. 4D, the signal processor 20 classifies the atrial fibrillation. The diagnostic system 10 preferably classifies atrial fibrillation into a variety of groups. This classification is useful for the clinical management of patients with atrial fibrillation. A patient in atrial fibrillation with a peak frequency of less than about 6.0 Hz has a substantially 100% probability to convert to normal sinus rhythm upon acute administration of ibutilide, whereas only about 28% of patients with a peak frequency above about 6.0 Hz will convert to normal sinus rhythm with the same treatment. A patient in atrial fibrillation with a peak frequency of less than about 6.5 Hz will have about 80% probability of remaining in normal sinus rhythm for more than about 3 months after an initial successful cardioversion, whereas a patient in atrial fibrillation with a peak frequency of more than about 6.5 Hz will have about 80% probability of recurrent atrial fibrillation within about 3 months after successful cardioversion.

Figure 6A:
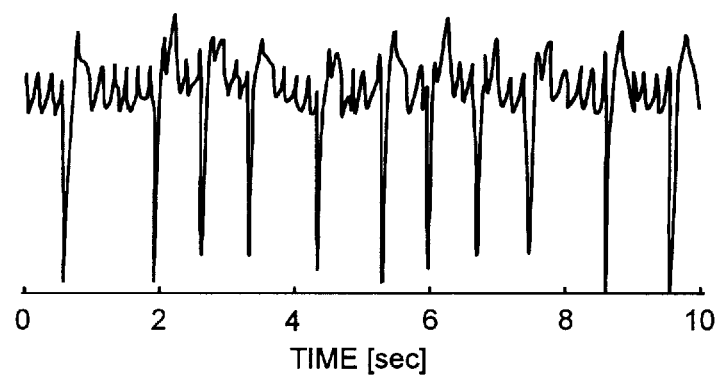
FIGS. 6A to 6C are examples of a signal from lead V1, a signal after bandpass filtering and subtraction of QRST, and a frequency power spectrum produced by Fourier transformation, respectively.
Figure 6B:
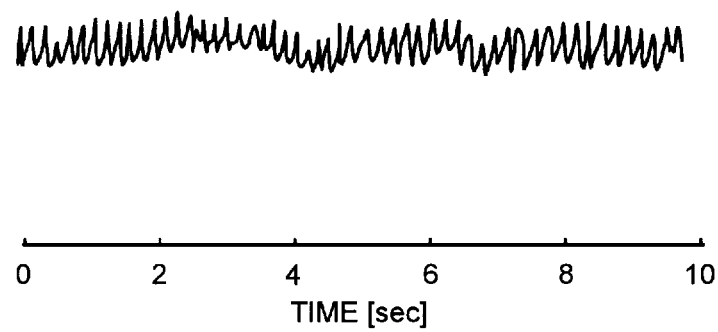
Figure 6C:
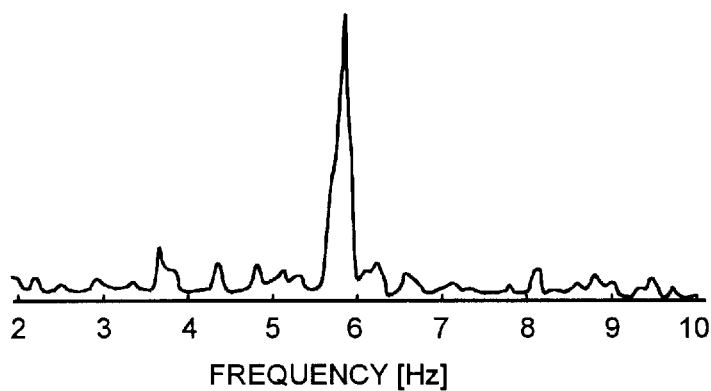

FIGS. 6A to 6C illustrate an example of a set of signals at various stages of processing by the diagnostic system 10. FIG. 6A depicts an example of a recording from ECG lead V1 12 with atrial fibrillation and rapid ventricular response. This signal is carried by the electrode 12 and is amplified and filtered by pre-amplifier circuit 14 and filter circuit 16. The signal processor 20, in summary, proceeds to detect the QRST complexes and to derive one or more templates for the QRST complexes. Each QRST complex is then removed by subtracting the appropriate template for that QRST complex. FIG. 6B provides an example of a fibrillatory baseline signal which has the QRST complexes removed using the template matching algorithm. The signal processor 20 then subjects the fibrillatory baseline signal to a Fourier transformation, with the result of the Fourier transformation being shown in FIG. 6C. As shown in FIG. 6C, most of the power is concentrated within a single narrow peak, which in this example, is centered approximately at 5.8 Hz.

In summary, applicants have determined the classes of atrial fibrillation and compared the results from the diagnostic system 10 with measurements from intra-atrial electrograms. The peak frequency of surface ECG leads V1, aVF, and V5 was compared to the peak frequency of the corresponding intraatrial electrograms using Pearson correlation. The median atrial cycle length measured on the intraatrial recordings was also compared to the peak frequency of the surface ECG using a correlation test. The mean peak-to-peak amplitude of the fibrillatory baseline (after QRST subtraction) was measured in lead V1. To minimize the confounding effects of gain setting and chest wall attenuation, amplitude was expressed as a percentage of the QRST magnitude. The relationship between frequency and this normalized amplitude was determined using Pearson correlations. The peak frequencies of the surface ECG in patients with induced, paroxysmal and chronic atrial fibrillation were compared using analysis of variance for repeated measures. The stability of peak frequency measurements at two different times and the relationship between right atrial and coronary sinus recordings were determined using Student's t—test for paired data. All results are presented as mean ± one standard deviation. A p value<0.05 was considered statistically significant.

Applicants have validated the signal processing technique used by the diagnostic system 10 to classify atrial fibrillation based on the frequency content of the atrial fibrillation. Most of the energy in the spectrum was contained within a single peak frequency that was highly correlated with the peak measured in simultaneous intraatrial electrograms, suggesting that it accurately reflected the median atrial rate during fibrillation. In patients with disparate rates in right and left atrial recordings, the surface ECG measurement was intermediate between the two or had separate peaks corresponding to the peaks in each atrium, suggesting that a single surface electrode derives its frequency content from a large portion of the atria. A clear relationship existed between the peak frequency of atrial fibrillation measured with diagnostic system 10 and the clinical behavior of the atrial fibrillation. Induced atrial fibrillation that terminated spontaneously within five minutes had a relatively low frequency. Induced atrial fibrillation that persisted or spontaneous atrial fibrillation less than three months in duration were intermediate in frequency. Chronic atrial fibrillation of greater than three months duration had the highest frequency.

Applicants have found that a direct relationship exists between the duration of chronic atrial fibrillation and the peak frequency recorded with the diagnostic system 10. This relationship is consistent with electrical remodeling and indicates that the technique is suitable for quantifying the magnitude of remodeling that has occurred in patients with persistent atrial fibrillation.

The technique employed by the diagnostic system 10 allows the peak frequency of fibrillatory activity to be quantified. This measurement correlates well with intraatrial cycle length, a parameter which appears to have primary importance in the genesis and perpetuation of atrial fibrillation. Thus, the frequency analysis result of the diagnostic system 10 is suitable for non-invasive assessment of the electrophysiologic state of the atria in patients with atrial fibrillation. Results of the present and previous studies using invasive monitoring show a clear relationship between fibrillation rate and the behavior of the arrhythmia. Low frequency fibrillation is more likely to terminate spontaneously or to respond to antiarrhythmic therapy, while high frequency fibrillation is more often persistent and drug refractory.

The techniques of the present invention are suitable for the prediction of conversion with ibutilide, for estimation of time to recurrence after cardioversion, and for prediction of left atrial thrombus on transesophageal echo.

The forgoing description of the preferred embodiment of the invention has been presented only for the purpose of illustration and description and is not intended to be exhaustive or to limit the invention to the precise form disclosed. Many modifications and variations are possible in light of the above teaching.

For example, the diagnostic system 10 may receive high level ECG signals from a conventional ECG machine. The electrodes 12, pre-amplifier circuit 14, and filter circuit 18 may comprise a conventional ECG machine and the remainder of the diagnostic system 10 may be housed in a separate enclosure. This separate enclosure, for instance, may comprise a computer having a Pentium processor, or other computer, equipped with an A/D board. Alternatively, the entire diagnostic system 10 may be enclosed integral with an ECG machine. For those ECG machines that have processing capability, the ECG machine may be converted to include the diagnostic system 10 with a software upgrade or a combination of a software and hardware upgrade.

The invention has been described with reference to a signal processor 20, peak frequency detector 19, transformation circuit 27, filter circuit 18, and controller 24. Each of these components may comprise a separate hard-wired circuit for performing its operations. Alternatively, the invention may be implemented with a microprocessor or digital signal processor for performing the functions of any one or more of the components.

The diagnostic system 10 is not limited to the use of one or more templates to subtract out the QRST complexes but may have a greater number of templates. By using more than two templates, the diagnostic system 10 may be able to more effectively remove a greater proportion of the QRST complexes and therefore derive a signal that more accurately reflects the fibrillatory baseline signal. For instance, the signal processor 20 may form a plurality of different templates by placing the first QRST complex within a first template and by comparing the second QRST complex to the first template. If, for instance, the second QRST complex conforms to within a certain degree to the first template, then the second QRST complex is placed within that template but otherwise forms a second template. Each subsequent QRST complex is compared to the existing templates and is either placed within one that provides the closest fit or forms an entirely new template. As will be apparent to those skilled in the art, the signal processor 20 can form these templates in a multitude of different ways, such as by generating new templates only for those QRST complexes which have a duration greater than 1.2 times the mean duration. Furthermore, the diagnostic system 10 may incorporate signal processing techniques that enable the entire removal of each QRST complex without the need for a template matching and subtraction algorithm.

The signal processor 20 and controller 24 may also act to provide additional file integrity and suitability checks. As described above with reference to step 88 in FIG. 5D, the signal processor 20 may determine whether the files are complete after the Fourier transformation at step 86. The invention may include additional checks to determine whether the signals should be processed, such as after the signals have been received, converted into digital signals, and filtered.

Also, the invention has been described with reference to electrodes 12 that are non-invasively applied externally to the surface of the patient P. In this manner, the invention processes electrical signals that represent the global response of the heart. The invention, however, may also operate with internal electrodes, such as electrode catheters. These internal electrodes may directly detect the fibrillatory baseline signal, thereby obviating the need for any signal processing to remove the QRST complexes. The invention can therefore classify atrial fibrillation based on signals detected with internal electrodes.

EXAMPLE 1

FREQUENCY ANALYSIS OF HUMAN ATRIAL FIBRILLATION WITH SURFACE ECG

Patient Selection and Recording Technique

Three groups of patients undergoing clinically-indicated electrophysiologic study were enrolled—those with no history of atrial fibrillation, patients with paroxysmal atrial fibrillation, and patients with chronic (>b 1month) persistent atrial fibrillation. None of these patients was taking antiarrhythmic or beta blocking drugs at the time of study. All patients with chronic atrial fibrillation had transthoracic echocardiograms within 3 months of the study. These patients were retrospectively reviewed and the left ventricular ejection fraction and left atrial diameter quantified using conventional techniques. Patients in sinus rhythm had atrial fibrillation induced using rapid right atrial pacing (cycle length 10 msec, 2–5 second duration). Recordings were made 30 to 60 seconds after induction of atrial fibrillation. In addition to the twelve lead electrocardiogram, endocardial recordings were made using conventional quadropolar electrode catheters with 1 cm interelectrode spacing from the superior right atrium and in a subset of patients from the mid coronary sinus as well.

Intraatrial recordings were obtained simultaneously with the surface ECG recordings during induced or spontaneous atrial fibrillation. In order to assess the accuracy of surface ECG frequency analysis, the frequency content of the intraatrial electrograms was quantified and compared to the value obtained from the surface ECG leads 12. Two techniques were used to quantify the fibrillation frequency of the intraatrial electrograms—atrial cycle length determinations and Fourier analysis. Each intraatrial recording was subjected to bandpass filtering using a third order, zero phase Butterworth filter at 40 to 250 Hz. A third order, zero phase low pass filter at 20 Hz was then applied to the absolute value of the resulting signal. Atrial activation was automatically detected on this filtered signal when the signal amplitude exceeded 5 to 10% of the maximal atrial electrogram amplitude found in the recording. The timing of atrial activation was defined as the local maximum for each atrial activation. To prevent double counting, an 80 msec refractory period was incorporated into the detection algorithm. The intra-atrial recordings were also subjected to Fourier transformation using methods comparable to those applied to the signals detected with surface electrodes 12; bandpass filtering having a pass-band of 0.5 Hz to 60 Hz, reduction of the sampling rate to 102 Hz, application of a Hamming window, and 1024 point discrete Fourier transformation.

Patient Population

A total of 54 recordings of atrial fibrillation was analyzed in 40 patients undergoing electrophysiology study. In 5/40 (12%), the ECG was inadequate for analysis. One of these was due to a ventricular response consistently above 160 beats per minute. In one other, preexcitation produced a broad QRST and a rapid ventricular response. In the three remaining patients frequent polymorphic ventricular ectopy prevented adequate template matching and subtraction of the QRST.

Table 1 summarizes the clinical characteristics of the 35 patients where ECG signals from electrodes 12 were analyzed. As expected, patients with no history of atrial fibrillation (n=18) were younger and less likely to have structural heart disease than those with paroxysmal (n=8) or chronic (n=9) atrial fibrillation. The majority of these patients were referred for ablation of paroxysmal supraventricular tachycardia, whereas 11/17 (65%) of patients with a history of atrial fibrillation were undergoing ablation of the atrioventricular junction.

TABLE 1

Characteristics of the Study Population

| | No History of AF n = 18 | Paroxysmal AF n = 8 | Chronic AF n = 9 |
|---|---|---|---|
| Male/Female | 11/7 | 4/4 | 6/3 |
| Age (years) | 45 ± 13 | 65 ± 13 | 66 ± 8 |
| Heart Disease | | | |
| None | 12 | 3 | 1 |
| CAD | 4 | 1 | 3 |
| VHD | | | 2 |
| HTN | 1 | 1 | 2 |
| DCM | 1 | 2 | 1 |
| HCM | | 1 | |
| EPS Indication | | | |
| AF | | 5 | 6 |
| AFl | 1 | 1 | |

TABLE 1-continued

Characteristics of the Study Population

|  | No History of AF n = 18 | Paroxysmal AF n = 8 | Chronic AF n = 9 |
|---|---|---|---|
| SVT | 10 | | |
| VT | 6 | 1 | 3 |
| Syncope | 1 | 1 | |
| LA size (mm) | | | 46 ± 5 |
| LVEF (%) | | | 46 ± 13 |
| AF Duration | | | |
| <3 months | | | 4 |
| >3 months | | | 5 |

AF = Atrial Fibrillation, AF1 = Atrial Flutter, CAD = Coronary Artery Disease, DCM = Dilated Cardiomyopathy, EPS = Electrophysiology Study, HCM = Hypertrophic Cardiomyopathy, HTN = Hypertension, LA = Left Atrium, LVEF = Left Ventricular Ejection Fraction, SVT = Supraventricular Tachycardia; VT = Ventricular Tachycardia, VHD = Valvular Heart Disease.

Frequency Spectrum of the Surface ECG in Atrial Fibrillation

The mean peak frequency of fibrillatory activity was 5.8±1.2 Hz (range 3.8 to 9.0) in lead V1, 5.7±1.2 Hz (range 3.5 to 9.0) in aVF and 5.7±1.0 Hz (range 3.9 to 8.7) in V5, respectively. There was a strong correlation between peak frequencies observed in V1 and aVF (r=0.97, p<0.0001) as well as between V1 and V5 (r=0.84, p<0.0001). Mean differences between these peak frequencies measured 0.19±0.21 Hz (range 0 to 0.80) and 0.37±0.52 Hz (range 0 to 2.33), respectively. Most of the power of the signal derived from the ECG was contained within a single sharp peak, as shown in FIG. 6C. The mean width of this peak (at 10% maximal amplitude) was 0.5±0.17 Hz. More than half of the total power of the signal (57±17%) was contained within±0.5 Hz of the peak frequency.

In lead V1, fibrillation amplitude was 4.9±3.2% of QRST amplitude and ranged w widely from 1.2 to 13%. A weak but statistically significant negative correlation existed between the normalized peak-to-peak amplitude of fibrillatory waves and frequency (r=0.36, p=0.01).

Comparison of Surface ECG and Endocardial Recordings

Figure 7:
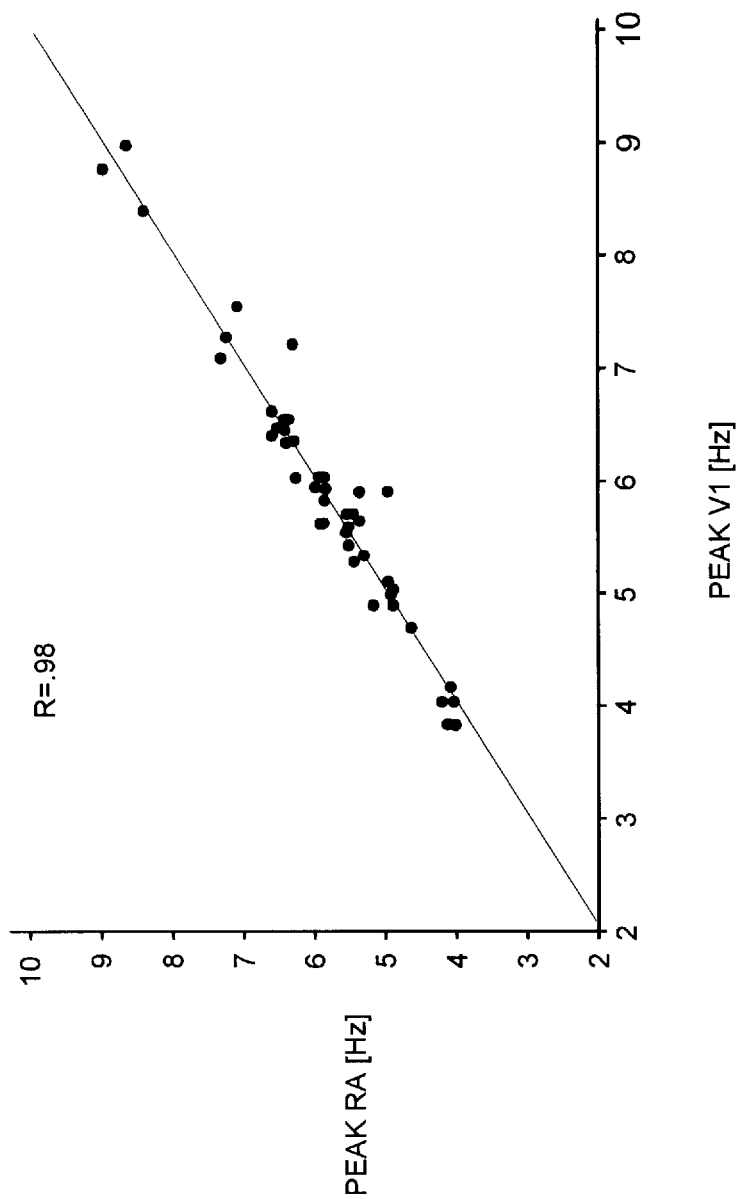
FIG. 7 is a plot of a peak frequency derived through analysis of an electrocardiogram according to preferred embodiment of systems according to the present the invention and from direct measurements from right atrial recordings.

The median fibrillatory cycle length recorded from the right atrium was 179±31 ms (range 112 to 257) and the mean peak frequency was 5.8±1.1 Hz (range 4.1 to 9.0). A strong negative correlation existed between median right atrial fibrillatory cycle length and surface lead V1 peak frequency and a strong positive correlation between right atrial and V1 peak frequencies, as shown by FIG. 7. Similar relationships existed between leads aVF and V5 and the intraatrial recordings, as shown below in Table 2.

TABLE 2

Correlation Coefficients and Average Discrepancies Between Right Atrial and Surface ECG Leads V1, aVF and V5

| ECG Lead | Correlation Coefficient | | Discrepancy Between RA-ECG | |
|---|---|---|---|---|
| | RA(median cycle length)-ECG | RA(peak frequency)-ECG | Mean [Hz] | Range [Hz] |
| V1 | −.91* | .98* | .15 ± .20 | 0–.87 |
| aVF | −.90* | .94* | .26 ± .28 | 0–1.13 |
| V5 | −.79* | .81* | .40 ± .53 | 0–2.00 |

RA = Right Atrium
*p < .001

Figure 8A:
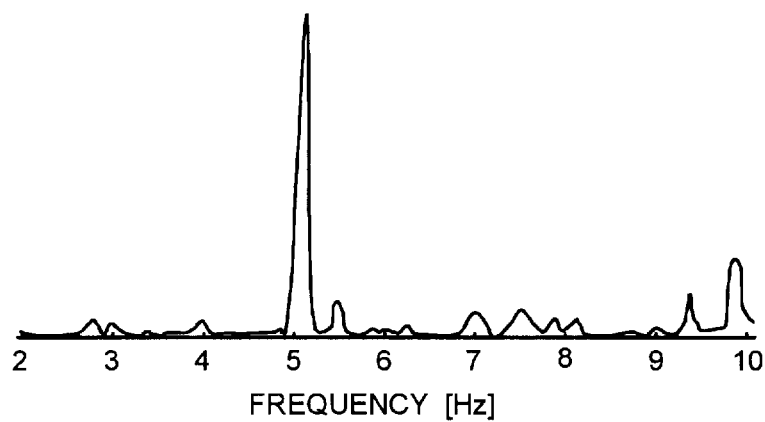
FIGS. 8A to 8C are examples of a frequency analysis for signals from the right atrium, the coronary sinus, and from lead VI, respectively.
Figure 8B:
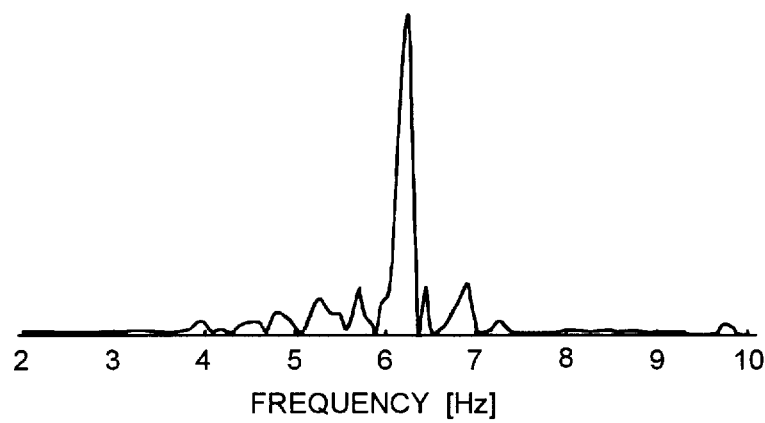
Figure 8C:
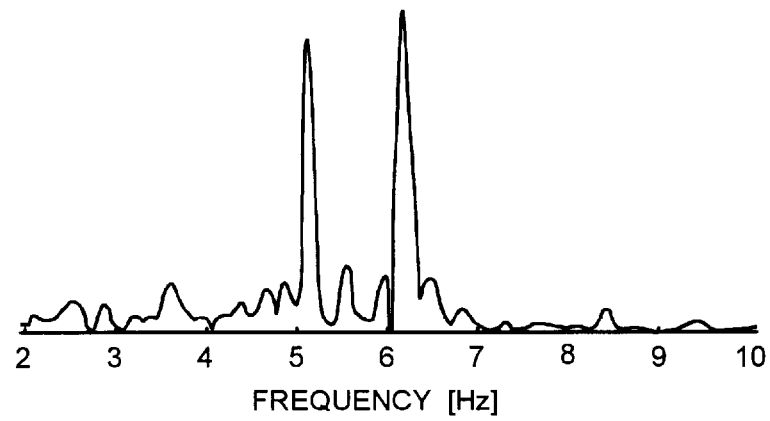

In 7 patients, a total of 10 simultaneous recordings from the right atrium and coronary sinus were made. The correlation coefficient between peak frequencies at these two sites was 0.75 (p=0.013) and the mean difference was 0.36±0.33 Hz (range 0 to 1.1). A strong correlation existed between the peak in fibrillatory frequency recorded in the coronary sinus and the peak frequency in lead V1 (r=0.93, p<0.0001), with a mean difference of 0.21±0.19 Hz (range 0 to 0.67). In 3 episodes the difference in the right and left atrial frequency during atrial fibrillation was greater than 0.5 Hz. Analysis of the surface ECG in these cases revealed peaks between the two intraatrial recordings or two peaks, each corresponding to one of the intraatrial signals, as shown by FIG. 8C.

Frequency Stability

The peak frequency detected after Fourier transformation is extremely stable. In a subset of 6 patients, recordings were made at two different times. No significant shift in peak frequency (6.1±1.2 vs. 6.3±1.1 Hz, p=0.634, mean change 0.5±0.2 Hz) was found over a period of 23±8 minutes.

Relationship Between Frequency and Clinical Characteristics

A significant relationship existed between the clinical behavior of atrial fibrillation episodes and the peak frequency recorded with diagnostic system 10 with electrodes 12. Episodes of induced atrial fibrillation that terminated spontaneously in less than 5 minutes (n=17) had a lower peak frequency than those persisting for longer periods (n=8) or chronic atrial fibrillation (n=9) (5.4±0.61 vs 6.7±1.3 vs 6.4±0.8 Hz, p<0.05).

Figure 11:
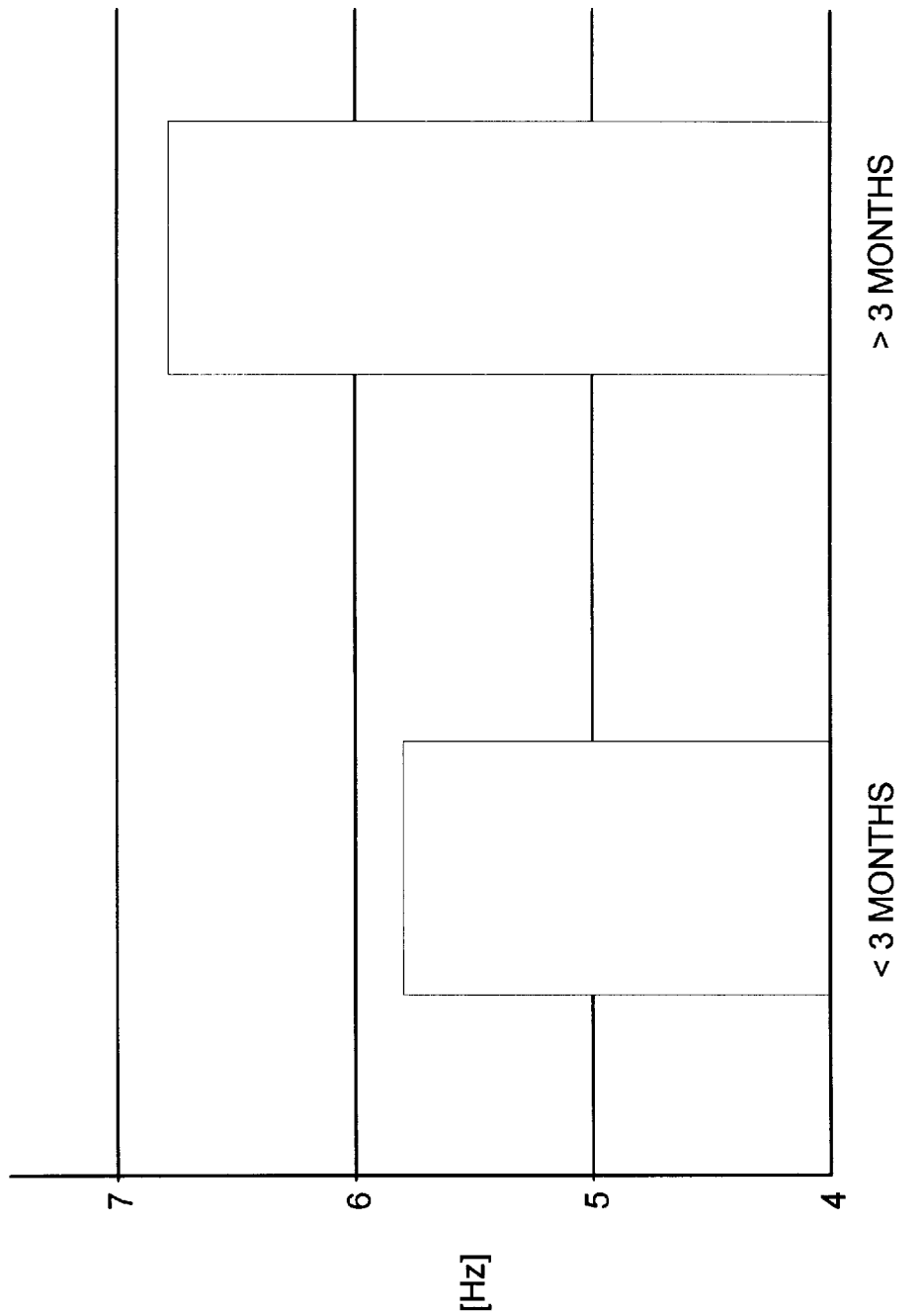
FIG. 11 is a bar graph depicting peak frequency for patients that had atrial fibrillation for less than three months and peak frequency for patients that had atrial fibrillation for greater than three months before the recording was made.

In the subset of patients with chronic atrial fibrillation, the duration of the arrhythmia appeared to affect the peak frequency. As reflected in the bar graph in FIG. 11, recordings from patients with atrial fibrillation less than 3 months in duration had a lower peak frequency than those where it had persisted for longer (5.8±0.5 vs 6.9±0.5 Hz, p=0.014). In contrast to frequency, fibrillation amplitude had no relation to the persistence or chronicity of the arrhythmia.

No other clinical variable including age, gender, body surface area, or type of heart disease affected the peak frequency measurement during atrial fibrillation. No relationship existed between left atrial diameter or left ventricular ejection fraction and peak frequency (r=0.37, p=0.36, r=7–16, p=0.70 respectively).

EXAMPLE 2

Prediction of Conversion with Ibutilide

In 12 patients (10 male, mean age 55±12 years) with persistent atrial fibrillation conversion to sinus rhythm was attempted using intravenous ibutilide. Patients had sustained arrhythmia for 5 minutes in induced episodes (n=5) and >24 hours (1 day to 3 months) in spontaneous episodes (n=7). Patients received a 30 minutes infusion of ibutilide fumarate (up to 2 mg). Continuous recording of a 12 lead surface ECG was performed beginning 10 minutes before the infusion and ending after 30 minutes after its completion. The surface ECG was stored on optical disc using a commercial recording system (Prucka Engineering Inc.). Ten second segments from lead V1 immediately prior to the to the begin of ibutilide infusion (n=12) and after every minute during infusion until completion of infusion or conversion to sinus rhythm (n=8) were then analyzed off-line using the diagnostic system 10. All continuous variables are expressed as mean value ± one standard deviation. The peak frequencies of the surface ECG in converters and non-converters were compared using Student's t-test. A p value of <05 was considered statistically significant.

Figure 9:
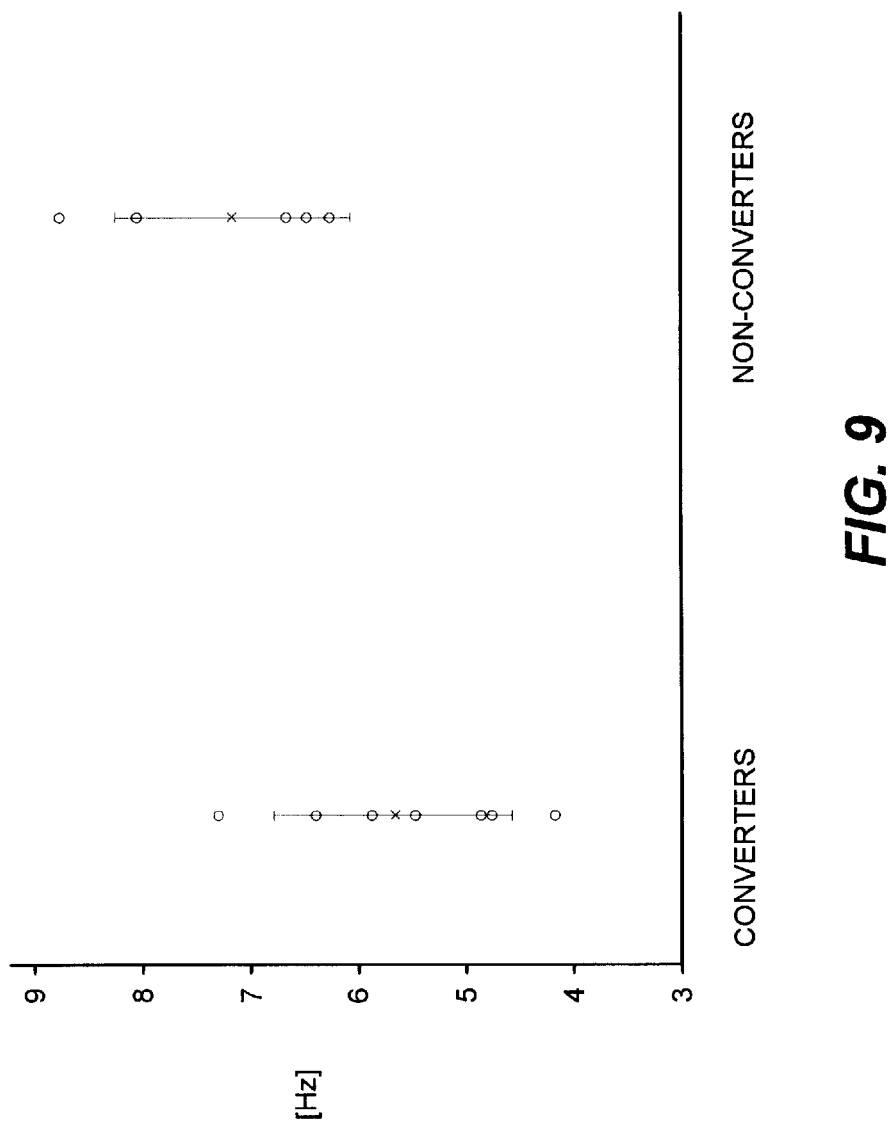
FIG. 9 is a plot of peak frequencies for those patients who converted over to a normal sinus rhythm with ibutilide and peak frequencies for those patients who did not convert to normal sinus rhythm with ibutilide.
Figure 10:
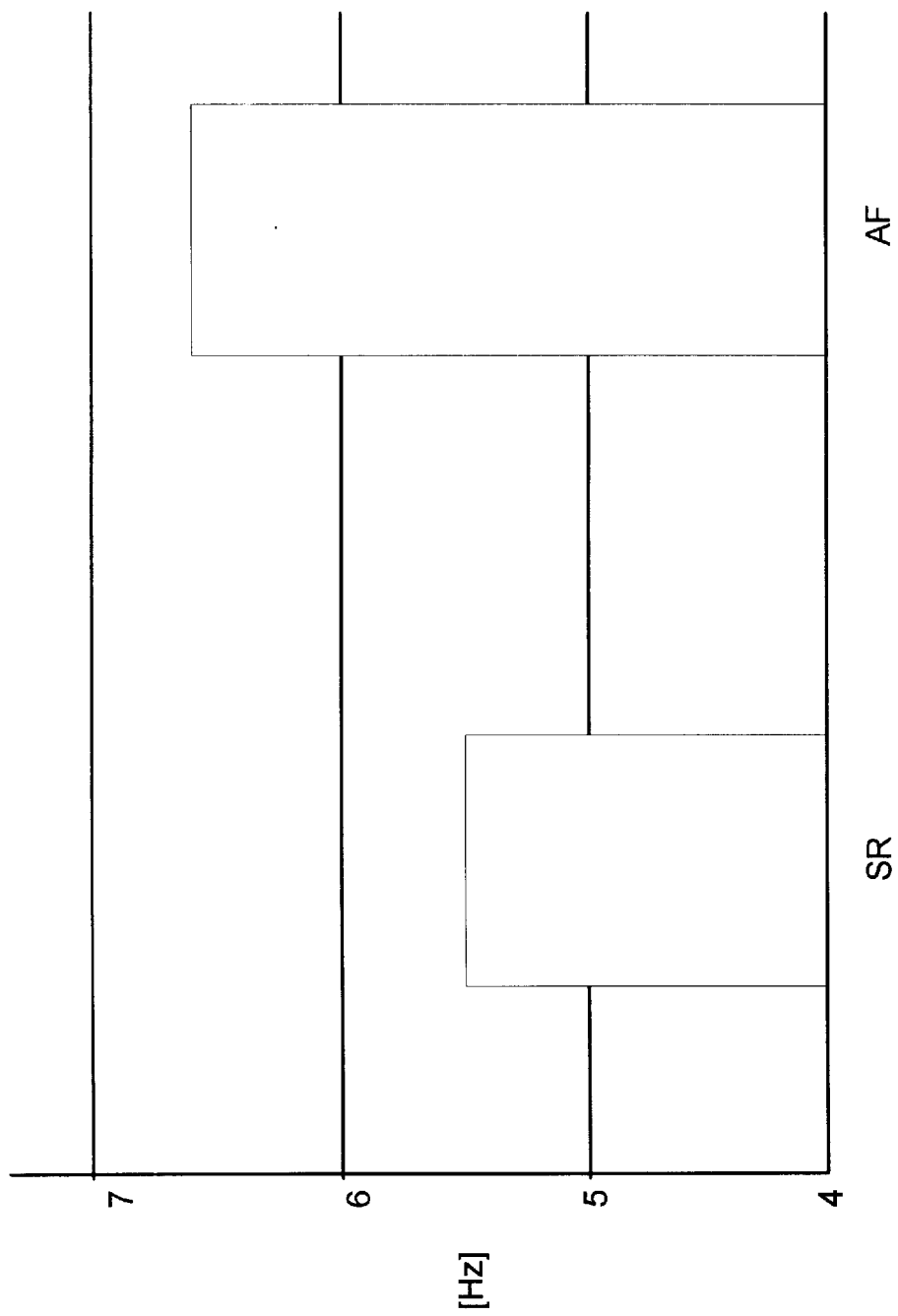
FIG. 10 is a bar graph depicting peak frequency for patients that stayed in normal sinus rhythm for 3 months after cardioversion and peak frequency for patients that had a recurrence of atrial fibrillation within 3 months after cardioversion.

Overall, atrial fibrillation was successfully terminated in 7/12 patients (58%). The mean time to termination was 15±12 minutes (5–45). Within the first 10 minutes after start of infusion 5/7 conversions were observed. Mean peak frequencies were 6.4±1.3 Hz (4.2 to 8.8) before and 4.5±1.0 Hz (3.1 to 6.1) after ibutilide infusion. Peak frequency was reduced in all patients ranging from 0.9 to 2.7 Hz. There was a statistically significant effect of peak frequency obtained prior to infusion on conversion success. Converters exhibited a mean peak frequency of 5.7±1.1 Hz as opposed to 7.2±1.1 Hz in non-converters (p=0.039). A reflected in the plot in FIG. 9, success rate was 100% in patients with peak frequency less than 6 Hz compared to 28% in patients with peak frequency above 6 Hz (p=0.013).

While the foregoing specification teaches the principles of the present invention, with examples provided for the purpose of illustration, it will be understood that the practice of the invention encompasses all of the usual variations, adaptations, or modifications, as come within the scope of the following claims and their equivalents.

What is claimed is:

1. A system for classifying atrial fibrillation, comprising:
   means for receiving electrical signals indicative of a heart's activity;
   means for processing the electrical signals to remove ventricular activity from the electrical signals and to output a fibrillatory baseline signal;
   means for transforming the fibrillatory baseline signal into a set of frequency domain signals;
   means for detecting a peak frequency within the set of frequency domain signals; and
   means for classifying atrial fibrillation based on the peak frequency.

2. The system as set forth in claim 1, wherein the receiving means comprises at least one electrode for being placed on an external surface of a patient with the electrode generating the electrical signals indicative of the heart's activity.

3. The system as set forth in claim 1, wherein the receiving means comprises at least one electrode for being placed within a patient for detecting the fibrillatory baseline signal.

4. The system as set forth in claim 1, wherein the receiving means comprises an interface for receiving digital signals indicative of the heart's activity.

5. The system as set forth in claim 4, wherein the interface receives the digital signals from a storage device.

6. The system as set forth in claim 4, wherein the interface receives the digital signals from a remote transmitter.

7. The system as set forth in claim 1, wherein the receiving means comprises an interface for receiving analog signals indicative of the heart's electrical activity.

8. The system as set forth in claim 1, wherein the interface receives the analog signals from an ECG machine.

9. The system as set forth in claim 1, wherein the means for processing the electrical signals comprises means for detecting QRST complexes in the electrical signals, means for generating one or more QRST templates, and means for subtracting QRST complexes using the one or more QRST templates.

10. The system as set forth in claim 9, wherein the means for generating the one or more templates averages the QRST complexes according to their duration in time.

11. The system as set forth in claim 1, wherein the fibrillatory baseline signal comprises a digital signal and the processing means compresses the fibrillatory baseline signal.

12. The system as set forth in claim 11, wherein the processing means applies a Hamming window when compressing the fibrillatory baseline signal.

13. The system as set forth in claim 1, wherein the means for transforming the fibrillatory baseline signal performs a Fourier transformation of the fibrillatory baseline signal to produce the set of frequency domain signals.

14. The system as set forth in claim 1, further comprising an analog-to-digital converter for converting the electrical signals into digital signals indicative of the heart's activity.

15. The system as set forth in claim 1, wherein the classifying means measures a maximum power level at the peak frequency.

16. The system as set forth in claim 15, wherein the classifying means measures a band of frequencies having power levels at or above a predetermined fraction of the maximum power level.

17. The system as set forth in claim 16, wherein the classifying means measures the band of frequencies having power levels at or above 10% that of the maximum power level.

18. The system as set forth in claim 1, wherein the classifying means measures a percentage of power of the frequency domain set of signals which is contained within a predetermined range of frequencies about the peak frequency.

19. The system as set forth in claim 18, wherein the classifying means measures the percentage of total power contained within±0.5 Hz of the peak frequency.

20. The system as set forth in claim 1, wherein the classifying means compares the peak frequency to a threshold frequency.

21. The system as set forth in claim 20, wherein the threshold frequency is 6.0 Hz.

22. The system as set forth in claim 1, further comprising means for indicating results from the classifying means.

23. An apparatus for classifying atrial fibrillation, comprising:
   a signal processor for receiving electrical signals indicative of a heart's activity, for removing ventricular activity from the electrical signals, and for outputting a fibrillatory baseline signal;
   a transformation circuit for receiving the fibrillatory baseline signal and for generating a set of frequency domain signals corresponding to the fibrillatory baseline signal; and
   a peak detector for detecting a peak frequency within the set of frequency domain signals;
   wherein the signal processor classifies the atrial fibrillation based on the peak frequency detected by the peak detector.

24. The apparatus as set forth in claim 23, further comprising at least one electrode for detecting the electrical signals indicative of the heart's activity and for supplying the electrical signals to the signal processor.

25. The apparatus as set forth in claim 24, wherein the electrode is for being placed on an external surface of a patient.

26. The apparatus as set forth in claim 24, wherein the electrode is for being placed within a patient for detecting the fibrillatory baseline signal.

27. The apparatus as set forth in claim 23, further comprising an interface for supplying digital signals indicative of the heart's activity to the signal processor.

28. The apparatus as set forth in claim 27, wherein the interface receives the digital signals from a storage device.

29. The apparatus as set forth in claim 27, wherein the interface receives the digital signals from a remote transmitter.

30. The apparatus as set forth in claim 23, further comprising an interface for receiving analog signals indicative of the heart's electrical activity.

31. The apparatus as set forth in claim 30, wherein the interface receives the analog signals from an ECG machine.

32. The apparatus as set forth in claim 23, wherein the signal processor detects QRST complexes in the electrical signals, generates one or more QRST templates, and subtracts QRST complexes using the one or more QRST templates.

33. The apparatus as set forth in claim 32, wherein the signal processor generates the one or more templates by averaging the QRST complexes according to their duration in time.

34. The apparatus as set forth in claim 23, wherein the fibrillatory baseline signal comprises a digital signal and the signal processor compresses the fibrillatory baseline signal.

35. The apparatus as set forth in claim 34, wherein the signal processor applies a Hamming window when compressing the fibrillatory baseline signal.

36. The apparatus as set forth in claim 23, wherein the transformation circuit performs a Fourier transformation of the fibrillatory baseline signal to produce the set of frequency domain signals.

37. The apparatus as set forth in claim 23, further comprising an analog-to-digital converter for converting the electrical signals into digital signals indicative of the heart's activity.

38. The apparatus as set forth in claim 23, wherein the signal processor classifies the atrial fibrillation by measuring a maximum power level at the peak frequency.

39. The apparatus as set forth in claim 38, wherein the signal processor classifies the atrial fibrillation by measuring a band of frequencies having power levels at or above a predetermined fraction of the maximum power level.

40. The apparatus as set forth in claim 39, wherein the signal processor classifies the atrial fibrillation by measuring the band of frequencies having power levels at or above 10% that of the maximum power level.

41. The apparatus as set forth in claim 23, wherein the signal processor classifies the atrial fibrillation by measuring a percentage of power of the frequency domain set of signals which is contained within a predetermined range of frequencies about the peak frequency.

42. The apparatus as set forth in claim 41, wherein the signal processor measures the percentage of total power contained within±0.5 Hz of the peak frequency.

43. The apparatus as set forth in claim 23, wherein the signal processor classifies the atrial fibrillation by comparing the peak frequency to a threshold frequency.

44. The apparatus as set forth in claim 43, wherein the threshold frequency is 6.0 Hz.

45. The apparatus as set forth in claim 44, wherein the signal processor indicates results of the classification of the atrial fibrillation.

46. A method for classifying atrial fibrillation, comprising the steps of:

receiving electrical signals indicative of a heart's activity;

processing the electrical signals to remove ventricular activity and to output a fibrillatory baseline signal;

transforming the fibrillatory baseline signal into a set of frequency domain signals;

detecting a peak frequency within the set of frequency domain signals; and classifying atrial fibrillation based on the peak frequency.

47. The method as set forth in claim 46, wherein the step of receiving comprises the step of placing at least one electrode on an external surface of a patient and detecting the electrical signals with the at least one electrode.

48. The method as set forth in claim 46, wherein the step of receiving comprises the step of placing the at least one electrode within a patient for detecting the fibrillatory baseline signal.

49. The method as set forth in claim 46, wherein the step of receiving comprises the step of receiving digital signals indicative of the heart's activity.

50. The method as set forth in claim 46, wherein the step of receiving comprises the step of receiving analog signals indicative of the heart's electrical activity.

51. The method as set forth in claim 46, wherein the step of processing comprises the steps of detecting QRST complexes in the electrical signals, generating one or more QRST templates, and subtracting QRST complexes using the one or more QRST templates.

52. The method as set forth in claim 46, wherein the fibrillatory baseline signal comprises a digital signal and the step of processing comprises a step of compressing the fibrillatory baseline signal.

53. The method as set forth in claim 52, wherein the step of processing comprises a step of applying a Hamming window.

54. The method as set forth in claim 46, wherein the step of transforming the fibrillatory baseline signal comprises a step of performing a Fourier transformation of the fibrillatory baseline signal to produce the set of frequency domain signals.

55. The method as set forth in claim 46, wherein the step of classifying comprises a step of measuring a maximum power level at the peak frequency.

56. The method as set forth in claim 55, wherein the step of classifying comprises a step of measuring a band of frequencies having power levels at or above a predetermined fraction of the maximum power level.

57. The method as set forth in claim 56, wherein the step of classifying comprises a step of measuring the band of frequencies having power levels at or above 10% that of the maximum power level.

58. The method as set forth in claim 46, wherein the step of classifying comprises a step of measuring a percentage of power of the frequency domain set of signals which is contained within a predetermined range of frequencies about the peak frequency.

59. The method as set forth in claim 58, wherein the step of classifying comprises a step of measuring the percentage of total power contained within±0.5 Hz of the peak frequency.

60. The method as set forth in claim 46, wherein the step of classifying comprises a step of comparing the peak frequency to a threshold frequency.

61. The method as set forth in claim 60, further including a step of indicating results of the step of classifying the atrial fibrillation.

62. The method as set forth in claim 46, wherein the step of classifying, a patient in atrial fibrillation with a peak frequency of less than about 6.0 Hz has a probability of substantially 100% to convert to normal sinus rhythm upon acute administration of ibutilide, whereas only about 28% of patients in atrial fibrillation with a peak frequency above about 6.0 Hz will convert to normal sinus rhythm upon acute administration of ibutilide.

63. The method as set forth in claim 46, wherein the step of classifying, a patient in atrial fibrillation with a peak frequency of less than about 6.5 Hz has about 80% probability of remaining in normal sinus rhythm for more than about 3 months after successful cardioversion, said cardioversion achieved by either electric shock or by intravenous administration of antiarrhythmic drugs.

64. The method as set forth in claim 46, wherein the step of classifying, a patient in atrial fibrillation with a peak frequency of more than about 6.5 Hz has about 80% probability of recurrent atrial fibrillation within about 3 months after successful cardioversion, said cardioversion achieved by either electric shock or by intravenous administration of antiarrhythmic drugs.

65. A computer-readable medium storing software for classifying atrial fibrillation, the software for use in performing the steps of:

receiving electrical signals indicative of a heart's activity;

processing the electrical signals to remove ventricular activity and to output a fibrillatory baseline signal;

transforming the fibrillatory baseline signal into a set of frequency domain signals; and detecting a peak frequency within the set of frequency domain signals.

66. The computer-readable medium as set forth in claim 65, further comprising a step of classifying the severity of the atrial fibrillation based on the peak frequency.

67. The computer-readable medium as set forth in claim 65, wherein the step of processing comprises the steps of detecting QRST complexes in the electrical signals, generating one or more QRST templates, and subtracting the QRST complexes using one or more of the QRST templates.

68. The computer-readable medium as set forth in claim 65, further comprising the step of indicating results of the step of classifying the atrial fibrillation.

69. The computer-readable medium as set forth in claim 66, wherein the step of classifying, a patient in atrial fibrillation with a peak frequency of less than about 6.0 Hz has a probability of substantially 100% to convert to normal sinus rhythm upon acute administration of ibutilide, whereas only about 28% of patients in atrial fibrillation with a peak frequency above about 6.0 Hz will convert to normal sinus rhythm upon acute administration of ibutilide.

70. The computer-readable medium as set forth in claim 66, wherein the step of classifying, a patient in atrial fibrillation with a peak frequency of less than about 6.5 Hz has about 80% probability of remaining in normal sinus rhythm for more than about 3 months after successful cardioversion, said cardioversion achieved by either electric shock or by intravenous administration of antiarrhythmic drugs.

71. The computer-readable medium as set forth in claim 66, wherein the step of classifying, a patient in atrial fibrillation with a peak frequency of more than about 6.5 Hz has about 80% probability of recurrent atrial fibrillation within about 3 months after successful cardioversion, said cardioversion achieved by either electric shock or by intravenous administration of antiarrhythmic drugs.

72. The computer-readable medium as set forth in claim 66, wherein the step of classifying comprises a step of measuring a maximum power level at the peak frequency.

73. The computer-readable medium as set forth in claim 66, wherein the step of classifying comprises a step of measuring a band of frequencies having power levels at or above a predetermined fraction of the maximum power level.

74. The computer-readable medium as set forth in claim 66, wherein the step of classifying comprises a step of measuring a percentage of power of the frequency domain set of signals which is contained within a predetermined range of frequencies about the peak frequency.

75. The computer-readable medium as set forth in claim 66, wherein the step of classifying comprises a step of comparing the peak frequency to a threshold frequency.

76. A method for determining suitable treatment for a patient with atrial fibrillation, comprising the steps of:

(a) detecting electrical signals recorded with electrocardiogram leads placed upon the patient, said signals indicative of the heart's electrical activity;

(b) processing the electrical signals to remove activity associated with ventricular activation and repolarization, by generating one or more templates for QRST complexes and subtracting one of the templates for each QRST complex with the detected electrical signals;

(c) performing a Fourier transformation, including a Hamming window, on the processed electrical signals to produce a set of frequency domain signals; and (d) detecting a peak frequency within the set of frequency domain signals.

77. The method as set forth in claim 76, wherein after the step (d) of detecting the peak frequency, a patient in atrial fibrillation with a peak frequency of less than about 6.0 Hz has a probability of substantially 100% to convert to normal sinus rhythm upon acute administration of ibutilide, whereas only about 28% of patients in atrial fibrillation with a peak frequency above about 6.0 Hz will convert to normal sinus rhythm upon acute administration of ibutilide.

78. The method as set forth in claim 76, wherein after the step (d) of detecting the peak frequency, a patient in atrial fibrillation with a peak frequency of less than about 6.5 Hz has about 80% probability of remaining in normal sinus rhythm for more than about 3 months after successful cardioversion, said cardioversion achieved by either electric shock or by intravenous administration of antiarrhythmic drugs.

79. The method as set forth in claim 76, wherein after the step (d) of detecting the peak frequency, a patient in atrial fibrillation with a peak frequency of more than about 6.5 Hz has about 80% probability of recurrent atrial fibrillation within about 3 months after successful cardioversion, said cardioversion achieved by either electric shock or by intravenous administration of antiarrhythmic drugs.

* * * * *

UNITED STATES PATENT AND TRADEMARK OFFICE
CERTIFICATE OF CORRECTION

PATENT NO.    : 5,772,604
DATED         : June 30, 1998
INVENTOR(S)  : Jonathan J. Langberg and Andreas Bollmann It is certified that error appears in the above-identified patent and that said Letters Patent is hereby corrected as shown below:

Column 5, line 12, delete "Hz are" and insert --Hz.--.

Column 10, line 1, delete "QRST," and insert --$QRST_1$--

Column 13, line 56, delete "(>b 1month)" and insert --(>1 month)--

Column 15, line 37, delete "w" after "ranged"

Signed and Sealed this

Twenty-seventh Day of June, 2000

*Attest:*

Q. TODD DICKINSON

*Attesting Officer*    Director of Patents and Trademarks